(12) United States Patent
Fadli

(10) Patent No.: US 9,107,848 B2
(45) Date of Patent: Aug. 18, 2015

(54) COUPLER WITH CATIONIC 7-AMINO-1,2,3,4-TETRAHYDROQUINOLINE STRUCTURE, DYEING COMPOSITION COMPRISING SAME, PROCESSES AND USES

(71) Applicant: L'OREAL, Paris (FR)

(72) Inventor: Aziz Fadli, Chelles (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/365,726

(22) PCT Filed: Dec. 17, 2012

(86) PCT No.: PCT/EP2012/075809
§ 371 (c)(1),
(2) Date: Jun. 16, 2014

(87) PCT Pub. No.: WO2013/087931
PCT Pub. Date: Jun. 20, 2013

(65) Prior Publication Data
US 2014/0352713 A1  Dec. 4, 2014

Related U.S. Application Data

(60) Provisional application No. 61/584,969, filed on Jan. 10, 2012.

(30) Foreign Application Priority Data

Dec. 16, 2011  (FR) ...................... 11 61793

(51) Int. Cl.
| | | |
|---|---|---|
| *A61Q 5/10* | (2006.01) | |
| *A61K 8/49* | (2006.01) | |
| *A61K 8/40* | (2006.01) | |
| *C07D 215/38* | (2006.01) | |
| *C07D 401/06* | (2006.01) | |
| *C07D 401/12* | (2006.01) | |

(52) U.S. Cl.
CPC ............ *A61K 8/4946* (2013.01); *A61K 8/40* (2013.01); *A61K 8/49* (2013.01); *A61K 8/494* (2013.01); *A61K 8/4926* (2013.01); *A61Q 5/10* (2013.01); *C07D 215/38* (2013.01); *C07D 401/06* (2013.01); *C07D 401/12* (2013.01); *A61K 2800/88* (2013.01)

(58) Field of Classification Search
CPC ...... A61Q 5/10; C07D 401/12; C07D 215/38; A61K 8/40; A61K 8/49; A61K 8/494; A61K 8/4926; A61K 8/4946; A61K 2800/88
USPC ............... 8/405; 132/314; 544/128; 546/171
See application file for complete search history.

(56) References Cited

U.S. PATENT DOCUMENTS

| | | |
|---|---|---|
| 4,003,699 A | 1/1977 | Rose et al. |
| RE30,199 E | 1/1980 | Rose et al. |
| 4,823,985 A | 4/1989 | Grollier et al. |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,708,151 A | 1/1998 | Mockli |
| 5,766,576 A | 6/1998 | Lowe et al. |
| 6,099,592 A | 8/2000 | Vidal et al. |
| 6,099,593 A | 8/2000 | Terranova et al. |
| 6,248,137 B1 | 6/2001 | Terranova et al. |
| 6,284,003 B1 | 9/2001 | Rose et al. |
| 6,338,741 B1 | 1/2002 | Vidal et al. |
| 6,645,258 B2 | 11/2003 | Vidal et al. |
| 6,730,789 B1 | 5/2004 | Birault et al. |
| 6,783,557 B1 | 8/2004 | Terranova et al. |

(Continued)

FOREIGN PATENT DOCUMENTS

| | | |
|---|---|---|
| DE | 2359399 A1 | 5/1975 |
| DE | 2941512 A1 | 4/1980 |

(Continued)

OTHER PUBLICATIONS

STIC Search Report dated Dec. 10, 2014.*
English absstract (Mar. 27, 2015) of the Patent No. DE 10103657 A1.*
International Search Report for PCT/EP2012/075809.
English language abstract for DE 10103657, (2002).
English language abstract for EP 0770375, (1997).
English language abstract for JP 2-19576, (1990).
English language abstract for JP 5-163124, (1993).

(Continued)

*Primary Examiner* — Eisa Elhilo
(74) *Attorney, Agent, or Firm* — The Marbury Law Group, PLLC

(57) ABSTRACT

The invention relates to the use of specific heterocyclic couplers which are cationic 7-amino-1,2,3,4-tetrahydroquinoline derivatives of formula (I) for dyeing keratin fibers such as the hair: in which formula (I): $R_1$ to $R_6$, $CAT^+$, $An^-$, and $R_a$ to $R_b$ are as defined in the description.

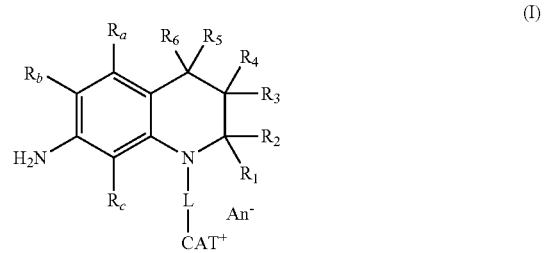

(I)

15 Claims, No Drawings

(56) References Cited

U.S. PATENT DOCUMENTS

| | | |
|---|---|---|
| 7,981,903 B2 | 7/2011 | Chamberlain et al. |
| 2001/0020310 A1 | 9/2001 | Terranova et al. |
| 2002/0050013 A1 | 5/2002 | Vidal et al. |
| 2003/0019051 A9 | 1/2003 | Vidal et al. |
| 2005/0166335 A1 | 8/2005 | Vidal et al. |
| 2006/0258689 A1 | 11/2006 | Kelly et al. |
| 2007/0136959 A1 | 6/2007 | Fadli |
| 2007/0143935 A1 | 6/2007 | Fadli et al. |
| 2008/0071092 A1 | 3/2008 | Vidal et al. |
| 2008/0234237 A1 | 9/2008 | Maddaford et al. |
| 2010/0115711 A1 | 5/2010 | Fadli et al. |
| 2010/0204196 A1 | 8/2010 | Chamberlain et al. |

FOREIGN PATENT DOCUMENTS

| | | |
|---|---|---|
| DE | 3843892 A1 | 6/1990 |
| DE | 4133957 A1 | 4/1993 |
| DE | 19543988 A1 | 5/1997 |
| DE | 10103657 A1 | 8/2002 |
| EP | 0714954 A2 | 6/1996 |
| EP | 0770375 A1 | 5/1997 |
| EP | 0926149 A1 | 6/1999 |
| EP | 1792606 A1 | 6/2007 |
| EP | 1792903 A1 | 6/2007 |
| FR | 2586913 A1 | 3/1987 |
| FR | 2733749 | 11/1996 |
| FR | 2801308 | 5/2001 |
| FR | 2866338 A1 | 8/2005 |
| FR | 2927078 A1 | 8/2009 |
| GB | 1026978 | 4/1966 |
| GB | 1153196 | 5/1969 |
| GB | 2036777 A | 7/1980 |
| JP | 219576 | 1/1990 |
| JP | 5163124 | 6/1993 |
| WO | 9408969 A1 | 4/1994 |
| WO | 9408970 A1 | 4/1994 |
| WO | 9501772 A1 | 1/1995 |
| WO | 9515144 A1 | 6/1995 |
| WO | 9615765 A1 | 5/1996 |
| WO | 9749378 A1 | 12/1997 |
| WO | 9847868 A1 | 10/1998 |
| WO | 0006146 A1 | 2/2000 |
| WO | 0043396 A1 | 7/2000 |
| WO | 03068749 A1 | 8/2003 |
| WO | 2005023807 A2 | 3/2005 |
| WO | 2008025240 A1 | 3/2008 |
| WO | 2009020990 A1 | 2/2009 |
| WO | 2009098257 A1 | 8/2009 |
| WO | 2011107501 A1 | 9/2011 |
| WO | 2011110627 A1 | 9/2011 |
| WO | WO 2011/110627 A1 * | 9/2011 .............. A61Q 5/10 |
| WO | 2013087932 A1 | 6/2013 |

OTHER PUBLICATIONS

Bilski, P.J. et. al., "Quenching and Generation of Singlet Oxygen by Hydroethidine and Related Chromophores," Chemical Physics Letters, Elsevier BV, NL., Jun. 16, 2009, vol. 475, No. 1-3, pp. 116-119.

* cited by examiner

COUPLER WITH CATIONIC 7-AMINO-1,2,3,4-TETRAHYDROQUINOLINE STRUCTURE, DYEING COMPOSITION COMPRISING SAME, PROCESSES AND USES

CROSS REFERENCE TO RELATED APPLICATIONS

This is a national stage application of PCT/EP2012/075809, filed internationally on Dec. 17, 2012, which claims priority to U.S. Provisional Application No. 61/584,969, filed on Jan. 10, 2012, as well as French Application No. 1161793, filed Dec. 16, 2011.

The subject of the present application is specific cationic 7-amino-1,2,3,4-tetrahydroquinoline derivatives, the use thereof for dyeing keratin fibres, in particular human keratin fibres such as the hair, the dyeing compositions comprising such cationic 7-amino-1,2,3,4-tetrahydroquinolines and also the processes and devices using these tetrahydroquinolines.

It is known practice to dye keratin fibres, and especially human hair, with dyeing compositions containing oxidation dye precursors, generally called oxidation bases, such as ortho- or para-phenylenediamines, ortho- or para-aminophenols and heterocyclic compounds. These oxidation bases are colourless or weakly coloured compounds which, when combined with oxidizing products, are able to produce coloured compounds by a process of oxidative condensation.

It is also known that the shades obtained with these oxidation bases can be varied by combining them with couplers or colouration modifiers, the latter being chosen more particularly from aromatic meta-diaminobenzenes, meta-aminophenols, meta-diphenols and certain heterocyclic compounds such as indole compounds.

The variety of the molecules used as oxidation bases and couplers allows a rich palette of colours to be obtained.

The "permanent" dyeing obtained by means of these oxidation dyes must moreover satisfy a certain number of requirements. Thus, it should have no toxicological drawbacks, it should allow shades to be obtained in the desired intensity, and it should show good resistance to external agents such as light, bad weather, washing, permanent-waving treatments, perspiration and rubbing.

The dyes are also required to cover white hairs, and to be as unselective as possible, that is to say to produce the smallest possible differences in colouration along a single lock of keratin fibre, which in general has a sensitivity (that is to say damage) which differs between its end and its root.

Heterocyclic oxidation bases make it possible to obtain a broad palette of colours, but combinations thereof with conventional couplers sometimes lack homogeneity and chromaticity and there is often considerable selectivity.

Certain non-cationic 7-amino-1,2,3,4-tetrahydroquinoline derivatives are known as dyes for polyesters (DE 294 1512). Other derivatives have been used for therapeutic application thereof (see, for example: vaniloid receptor modulator: WO 2003/068749; $5HT_{1A}$, $5HT_{1B}$, $HM_{1D}$ receptor antagonists: WO 98/47868; capsaicin receptor modulator: WO 2005/023807, NO inhibitor: US20080234237, and CCR5 receptor agonist or antagonist: WO 00/06146).

In hair dyeing, it is known practice to use non-cationic 7-amino-1,2,3,4-tetrahydroquinoline derivatives as couplers (WO 2008/025240). Nevertheless, the colourations obtained with these couplers are not always satisfactory. Indeed, whether in terms of solubility, of colour uptake, of chromaticity, of fastness, of persistence (washing, bad weather, light) and/or of colour selectivity (root/end colour "homogeneity"), these couplers do not always give the user satisfaction.

These technical problems have been solved by the use of specific heterocyclic couplers which are cationic 7-amino-1,2,3,4-tetrahydroquinoline derivatives of formula (I), for dyeing keratin fibres such as the hair;
compound of formula (I) and also the salts thereof with an organic or inorganic acid or base, the optical or geometric isomers thereof and/or the solvates thereof such as the hydrates:

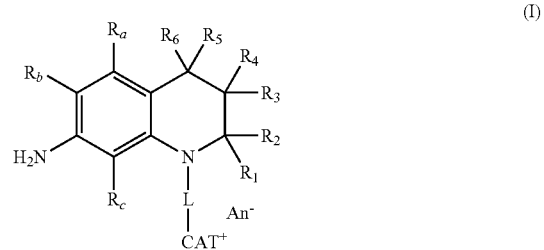

in which formula (I):
$R_1$, $R_2$, $R_3$, $R_4$, $R_5$ and $R_6$, which may be identical or different, represent a hydrogen or halogen atom; a linear or branched $C_1$-$C_6$ alkyl radical optionally substituted with one or more hydroxyl groups, preferably with a single hydroxyl group; a carboxyl radical; a ($C_1$-$C_6$) alkoxycarbonyl radical —C(O)—O—R with R representing a linear or branched $C_1$-$C_6$ alkyl radical; an alkylcarbonyloxy radical —O—C(O)—R with R being as defined previously; preferably, $R_1$, $R_2$, $R_3$, $R_4$, $R_5$ and $R_6$, which may be identical or different, represent a hydrogen atom or a $C_1$-$C_4$ alkyl radical; even more advantageously, $R_1$, $R_2$, $R_3$, $R_4$, $R_5$ and $R_6$ are identical and represent a hydrogen atom;

$R_a$, $R_b$ and $R_c$, which may be identical or different, represent a hydrogen or halogen atom or a $C_1$-$C_6$ alkyl radical; preferably, $R_a$, $R_b$ and $R_c$ are identical and represent a hydrogen atom;

L represents a saturated or unsaturated, linear or branched $C_1$-$C_{30}$, divalent hydrocarbon-based chain, optionally interrupted with one or more divalent groups or combinations thereof chosen from —N($R_d$)—, —O—, —S—, —C(O)— and —S(O)$_2$— with $R_d$ chosen from a hydrogen, and a $C_1$-$C_6$ alkyl, hydroxy($C_1$-$C_6$)alkyl or amino ($C_1$-$C_6$)alkyl radical; preferably, L represents a preferably saturated, and linear or branched, $C_1$-$C_{20}$ divalent hydrocarbon-based chain, which is optionally substituted in particular with one or more hydroxyl radicals, and/or optionally interrupted with one or more non-adjacent heteroatoms, such as oxygen or non-adjacent divalent amino radicals —N(R')—, R' denoting a hydrogen atom or a linear or branched $C_1$-$C_6$ alkyl radical;

$CAT^+$ represents a cationic radical in particular chosen from:
  a monocyclic or polycyclic, saturated or unsaturated, aromatic or nonaromatic, cationic heterocyclic radical, optionally substituted preferably with one or more radicals, which may be identical or different, preferably chosen from linear or branched $C_1$-$C_4$ alkyl radicals or $C_1$-$C_4$ hydroxyalkyl radicals;
  an ammonium radical $R_7R_8R_9N^+$—, with $R_7$, $R_8$ and $R_9$, which may be identical or different, representing a linear or branched ($C_1$-$C_6$)alkyl group, which is optionally substituted, preferably with one or more hydroxyl groups;
  an aryl radical with an exocyclic cationic charge;

An⁻ represents one or more anionic counterions, it being understood that there are as many anionic counterion(s), which may be identical or different, as there are cationic charge(s) in order to ensure electroneutrality of the molecule of formula (I).

A subject of the invention is also a process for dyeing keratin fibres using the compounds of formula (I) as defined previously.

A subject of the invention is also novel cationic heterocyclic couplers which are 7-amino-1,2,3,4-tetrahydroquinoline derivatives of formula (I) as defined previously.

A subject of the invention is also a process for synthesizing novel compounds of formula (I), and also a cosmetic composition comprising the compounds of formula (I) as defined previously.

A subject of the invention is also a multi-compartment kit or device comprising at least one compound of formula (I) as defined previously.

The couplers according to the invention result in a wide range of colours in oxidation dyeing. These couplers make it possible in particular to expand the colour range while improving the innocuousness of the oxidation dyeing couplers. In addition, these cationic 7-amino-1,2,3,4-tetrahydroquinoline derivatives make it possible to obtain colourations in varied shades, in particular dark, natural, natural dark, powerful and chromatic shades.

These colourations are also sparingly selective and they are persistant; they withstand well the various attacks that the fibres may experience.

These heterocyclic couplers exhibit, furthermore, a high solubility, which allows a satisfactory uptake of the colour.

Other characteristics, aspects, subjects and advantages of the present invention will emerge even more clearly on reading the description and the examples that follow.

In the following, and unless otherwise indicated:
the limits of a range of values are included in this range, in particular in the expressions "between" and "ranging from . . . to . . . ";
the expression "at least one" is equivalent to the expression "one or more";
"cationic heterocycle" or "cationic heterocyclic" radical is intended to mean preferably a cyclic radical comprising from 5 to 14 ring members, and from 1 to 5 heteroatoms such as O, S, N, or Se, and comprising at least one endocyclic or exocyclic cationic charge; more preferentially, said heterocyclic radical is mono- or bicyclic, comprising from 5 to 10 ring members and from 1 to 3 heteroatoms chosen from N, O and S, particularly N and O, for instance imidazoliums, pyridiniums, piperaziniums, pyrrolidiniums, morpholiniums, pyrimidiniums, thiazoliums, benzimidazoliums, benzothiazoliums, oxazoliums, benzotriazoliums, pyrazoliums, triazoliums, benzoxazoliums, piperidiniums;
"heterocycle" or "heterocyclic" radical is intended to mean a non-cationic cyclic radical comprising preferably from 5 to 14 ring members, and from 1 to 5 heteroatoms such as O, S, N, or Se; more preferentially, said heterocyclic radical is mono- or bicyclic, comprising from 5 to 10 ring members and from 1 to 3 heteroatoms chosen from N, O and S, particularly N and O, for instance imidazolyls, pyridinyls, piperazinyls, pyrrolidinyls, morpholinyls, pyrimidinyls, thiazolyls, benzimidazolyls, benzothiazolyls, oxazolyls, benzotriazolyls, pyrazolyls, triazolyls, benzoxazolyls, piperidinyls;
the "heterocyclic" radicals can be substituted with at least one substituent borne by a carbon atom, chosen from:

a $C_1$-$C_8$ alkyl radical optionally substituted with one or more radicals chosen from the following radicals: hydroxyl, $C_1$-$C_2$ alkoxy, $C_2$-$C_4$ (poly)hydroxyalkoxy, acylamino, amino substituted with two $C_1$-$C_4$ alkyl radicals, which may be identical or different, optionally bearing at least one hydroxyl group, or the two radicals possibly forming, with the nitrogen atom to which they are attached, a saturated or unsaturated, optionally substituted 5- to 7-membered and preferably 5- or 6-membered heterocycle optionally comprising another heteroatom identical to or different from nitrogen;
a halogen atom;
a hydroxyl group;
a $C_1$-$C_2$ alkoxy radical;
a (poly)hydroxy($C_2$-$C_4$)alkoxy radical;
an amino radical;
an amino radical substituted with one or two identical or different $C_1$-$C_6$ alkyl radicals, optionally bearing at least:
i) one hydroxyl group,
ii) one amino group optionally substituted with one or two optionally substituted $C_1$-$C_3$ alkyl radicals, it being possible for said alkyl radicals to form, with the nitrogen atom to which they are attached, a saturated or unsaturated and optionally substituted 5- to 7-membered heterocycle optionally comprising at least one other heteroatom identical to or different from nitrogen,
iii) one quaternary ammonium group —N⁺R'R"R'", M⁻ for which R', R" and R'", which may be identical or different, represent a hydrogen atom, or a $C_1$-$C_4$ alkyl group; and M⁻ represents the counterion of the corresponding organic acid, inorganic acid or halide,
an acylamino radical (—NR—C(O)—R') in which the radical R is a hydrogen atom or a $C_1$-$C_4$ alkyl radical optionally bearing at least one hydroxyl group and the radical R' is a $C_1$-$C_2$ alkyl radical;
a carbamoyl radical ((R)₂N—C(O)—) in which the radicals R, which may be identical or different, represent a hydrogen atom or a $C_1$-$C_4$ alkyl radical optionally bearing at least one hydroxyl group;
an alkylsulfonylamino radical (R'—S(O)₂—N(R)—) in which the radical R represents a hydrogen atom or a $C_1$-$C_4$ alkyl radical optionally bearing at least one hydroxyl group and the radical R' represents a $C_1$-$C_4$ alkyl radical, or a phenyl radical;
an aminosulfonyl radical ((R)₂N—S(O)₂—) in which the radicals R, which may be identical or different, represent a hydrogen atom or a $C_1$-$C_4$ alkyl radical optionally bearing at least one hydroxyl group,
a carboxylic radical in acid form or salified form (preferably with an alkali metal or a substituted or unsubstituted ammonium);
a cyano group;
a nitro or nitroso group;
a polyhaloalkyl group, preferentially trifluoromethyl;
alkoxycarbonyl (R-G-C(O)—) in which the radical R is a $C_1$-$C_4$ alkoxy radical, G is an oxygen atom or an amino group optionally substituted with a $C_1$-$C_4$ alkyl group itself optionally bearing at least one hydroxyl group, said alkyl radical possibly forming with the nitrogen atom to which they are attached a saturated or unsaturated, optionally substituted 5- to 7-membered heterocycle, optionally comprising at least one other heteroatom identical to or different from nitrogen;

the nonaromatic part of the heterocyclic radical may also be substituted with one or more oxo groups;

a hydrocarbon-based chain is unsaturated when it comprises one or more double bonds and/or one or more triple bonds;

an "aryl" radical represents a fused or non-fused monocyclic or polycyclic carbon-based group comprising from 6 to 22 carbon atoms, and in which at least one ring is aromatic; preferentially, the aryl radical is a phenyl, biphenyl, naphthyl, indenyl, anthracenyl or tetrahydronaphthyl;

a "cationic heterocyclic radical" is a heterocyclic group as defined previously, which comprises at least one quaternized endocyclic or exocyclic cationic group;

the term "cationic radical $Cat^+$" is intended to mean a cationic radical which is not modified by the pH, i.e. which is not a protonated radical such as $*-L-Cat^+-H$, which, in an alkaline medium, would no longer be cationic;

when the cationic charge is endocyclic, it is included in the electron delocalization via the mesomeric effect if the ring is aromatic, for example it is a pyridinium, imidazolium, pyrazolium, indolinium or benzimidazolium group:

or else it is on the heteroatoms of the ring members of the heterocycle, for example it is piperazinium, piperidinium, morpholinium, pyrrolinium or azepanium,

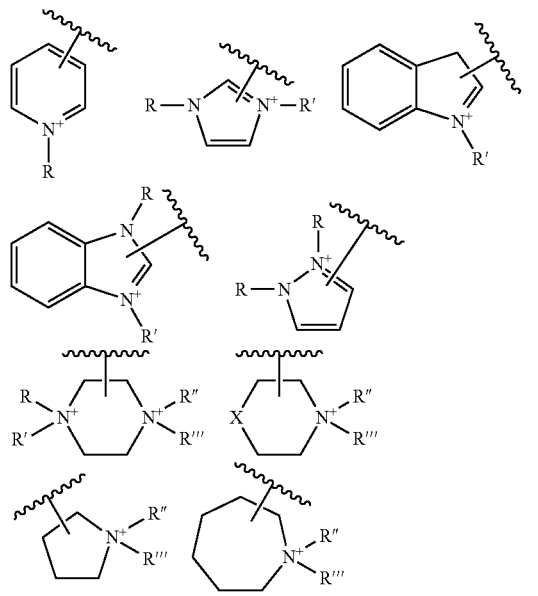

with R, R', R" and R''' being a heterocycle substituent as defined previously and particularly a (hydroxy)($C_1$-$C_8$) alkyl group such as methyl, and X representing O, or N(R) with R as defined previously;

when the cationic charge is exocyclic, the charge is on the outside of the ring and is not on one of the heteroatoms of the ring members of the heterocycle, for example it is an ammonium $R^+$ substituent, such as tri($C_1$-$C_6$)(hydroxy)alkylammonium, for instance methylammonium, which is on the outside of the heteroaryl, such as pyridinyl, indolyl, imidazolyl, piperazinyl, piperidinyl, morpholinyl, pyrrolyl and azepanyl:

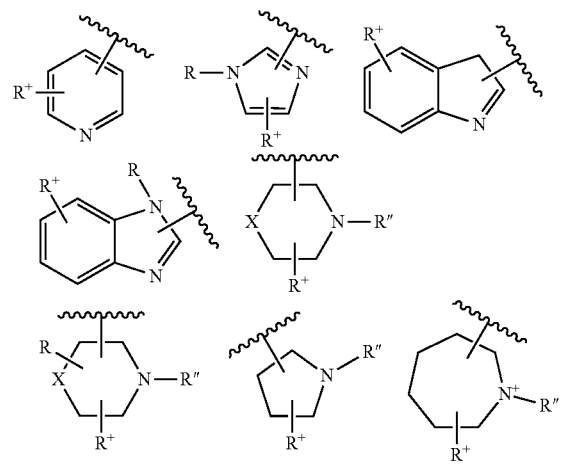

with R and R" being a substituent of a heterocycle as defined previously and $R^+$ an ammonium group $R_aR_bR_cN^+$—, or an ammonium group $R_aR_bR_cN^+$-($C_1$-$C_6$)alkylamino with $R_a$, $R_b$ and $R_c$, which may be identical or different, representing a hydrogen atom or a linear or branched ($C_1$-$C_6$)alkyl group, which is optionally substituted, preferably with one or more hydroxyl groups, such as methyl;

the term "cationic aryl with an exocyclic charge" is intended to mean an aryl ring of which the quaternized cationic group is on the outside of said ring; it is in particular an $R^+$ ammonium substituent such as $R_7R_8R_9N^+$—, with $R_7$, $R_8$ and $R_9$, which may be identical or different, representing a linear or branched ($C_1$-$C_6$)alkyl group, which is optionally substituted, preferably with one or more hydroxyl groups, on the outside of the aryl, such as phenyl or naphthyl, preferably phenyl:

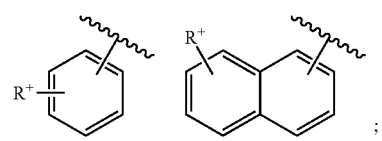

it being possible for said cationic aryl to also be optionally substituted with an atom or group as defined previously;

an "alkyl radical" is a linear or branched $C_1$-$C_{20}$ and preferably $C_1$-$C_8$ hydrocarbon-based radical;

the hydrocarbon-based chain may be unsaturated, and is preferably an "alkenylene radical" which is an unsaturated hydrocarbon-based divalent radical which may contain from 1 to 4 conjugated or unconjugated —C=C— double bonds; in particular, the alkenylene group contains 1 or 2 unsaturation(s);

the expression "optionally substituted" attributed to the $C_1$-$C_{30}$ divalent hydrocarbon-based chain or alkyl radical implies that said alkyl radical or hydrocarbon-based chain may be substituted with one or more radicals chosen from the following radicals: i) hydroxyl, ii) $C_1$-$C_4$ alkoxy, iii) acylamino, iv) amino optionally substituted with one or two identical or different $C_1$-$C_4$ alkyl radicals, said alkyl radicals possibly forming with the nitrogen atom that bears them a 5- to 7-membered heterocycle, optionally comprising another heteroatom identical to or different from nitrogen; v) or a quaternary ammonium group —$N^+R'R''R'''$, $M^-$ for which R', R'' and R''', which may be identical or different, represent a hydrogen atom or a $C_1$-$C_4$ alkyl group, or else —$N^+R'R''R'''$, forms a heteroaryl such as imidazolium optionally substituted with a $C_1$-$C_4$ alkyl group, and $M^-$ represents the counterion of the corresponding organic or inorganic acid or halide;

an "alkoxy radical" is an alkyloxy radical for which the alkyl radical is a linear or branched $C_1$-$C_{16}$ and preferentially $C_1$-$C_8$ hydrocarbon-based radical;

when the alkoxy group is optionally substituted, this implies that the alkyl group is optionally substituted as defined hereinabove;

an "anionic counterion" is an anion or an anionic group associated with the cationic charge(s) of the compound of formula (I).

Compound of Formula (I)

The present invention relates to cationic 7-amino-1,2,3,4-tetrahydroquinoline derivatives of general formula (I) as defined previously, and also the salts thereof with an organic or inorganic acid or base, the optical or geometric isomers thereof and/or the solvates thereof such as the hydrates.

According to one preferred embodiment of the invention, the compounds of formula (I) are such that the $CAT^+$ radical represents a monocyclic or bicyclic, saturated or unsaturated, aromatic or nonaromatic cationic heterocyclic radical, optionally substituted preferably with one or more radicals, which may be identical or different, preferably chosen from linear or branched $C_1$-$C_4$ alkyl radicals or $C_1$-$C_4$ hydroxyalkyl radicals. The heterocyclic radical comprises more particularly one or more endocyclic cationic charges, preferably one or two endocyclic cationic charges.

According to one variant, the $CAT^+$ radical is a saturated cationic heterocyclic radical such as pyrrolinium, piperidinium, morpholinium, piperazinium or piperazinedium, preferably substituted on at least one heteroatom with one or two ($C_1$-$C_4$)alkyl groups. According to another variant, the $CAT^+$ radical is an unsaturated cationic, preferably aromatic, heterocyclic radical such as imidazolium, preferably substituted on at least one heteroatom with one or two ($C_1$-$C_4$)alkyl groups.

According to another preferred embodiment of the invention, the compounds of formula (I) are such that the $CAT^+$ radical represents $R_7R_8R_9N^+$—, and in particular represents a tri(hydroxy)($C_1$-$C_4$)alkylammonium group, for instance trimethylammonium, triethylammonium, dimethylethylammonium, diethylmethylammonium, diisopropylmethylammonium, diethylpropylammonium, 2-hydroxyethyldiethylammonium, di-beta-hydroxyethylmethylammonium, tri-beta-hydroxyethylammonium, dimethylhydroxyethylammonium or 2-hydroxyethyldimethylammonium.

According to one particular embodiment of the invention, the compounds of formula (I) have the following structure (II):

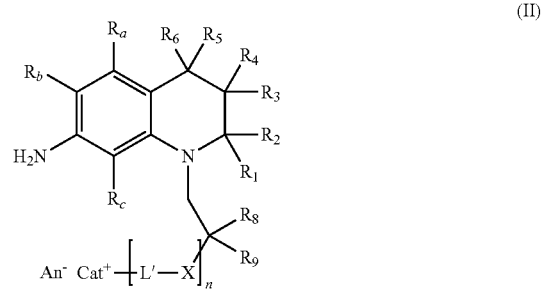

in which formula (II):

$R_a$, $R_b$, $R_c$, $R_1$, $R_2$, $R_3$, $R_4$, $R_5$ and $R_6$ and $CAT^+$ and $An^-$ have the same meaning as previously;

$R_8$ and $R_9$ independently represent a hydrogen atom or a $C_1$-$C_6$ alkyl radical optionally substituted in particular with an OH or interrupted with an oxygen atom; preferably $R_8$ and $R_9$ represent a hydrogen atom;

X represents an oxygen atom or an —N(R')— radical in which R' represents a hydrogen atom or a $C_1$-$C_4$ alkyl radical; preferably, R' represents H or $CH_3$;

L' represents a linear or branched and saturated divalent $C_1$-$C_{10}$ hydrocarbon-based chain, optionally substituted with one or more hydroxyl radicals; preferably, L' represents a linear or branched and saturated $C_1$-$C_6$ hydrocarbon-based chain, optionally substituted with one or more hydroxyl radicals; more particularly, L' represents a linear, saturated $C_1$-$C_4$ hydrocarbon-based chain;

n is 0, 1, 2, 3 or 4; in particular, n is 0, 1 or 2; preferably, n=0 or 1; it being understood that, when n is greater than or equal to 2, the radicals X respectively L' are identical or different.

The compounds of formula (I) may be in the form of a salt with an organic or inorganic acid or base.

The term "salt with an organic or inorganic acid" is intended to mean more particularly those chosen from addition salts with a cosmetically acceptable acid, such as the acidifying agents as defined hereinafter, for instance the salts derived i) from hydrochloric acid HCl, ii) from hydrobromic acid HBr, iii) from sulfuric acid $H_2SO_4$, iv) from alkylsulfonic acids: Alk-S(O)$_2$OH such as methylsulfonic acid and ethylsulfonic acid; v) from arylsulfonic acids: Ar—S(O)$_2$OH such as benzenesulfonic acid and toluenesulfonic acid; vi) from citric acid; vii) from succinic acid; viii) from tartaric acid; ix) from lactic acid; x) from alkoxysulfinic acids: Alk-O—S(O)OH such as methoxysulfinic acid and ethoxysulfinic acid; xi) from aryloxysulfinic acids such as tolueneoxysulfinic acid and phenoxysulfinic acid; xii) from phosphoric acid $H_3PO_4$; xiii) from acetic acid $CH_3C(O)OH$; xiv) from triflic acid $CF_3SO_3H$ and xv) from tetrafluoroboric acid $HBF_4$. More particularly, the compounds of formula (I) are optionally salified with strong inorganic acids, such as HCl, HBr, $H_2SO_4$ or $H_3PO_4$, or organic acids, for instance acetic acid, lactic acid, tartaric acid, citric acid, succinic acid, benzenesulfonic acid, para-toluenesulfonic acid, formic acid or methanesulfonic acid.

The term "salt with an organic or inorganic base" is intended to mean more particularly those chosen from addition salts with a cosmetically acceptable base, such as the alkalinizing agents as defined below, for instance alkali metal hydroxides such as sodium hydroxide or potassium hydroxide, aqueous ammonia, amines or alkanolamines.

In particular, the anionic counterion(s) is (are) chosen from i) halides such as chloride or bromide; ii) nitrates; iii) sulfonates, including $C_1$-$C_6$ alkylsulfonates: Alk-S(O)$_2$O$^-$ such as methylsulfonate or mesylate, and ethylsulfonate; iv) arylsulfonates: Ar—S(O)$_2$O$^-$ such as benzenesulfonate and toluenesulfonate or tosylate; v) citrate; vi) succinate; vii) tartrate; viii) lactate; ix) alkyl sulfites: Alk-O—S(O)O$^-$ such as methyl sulfite and ethyl sulfite; x) aryl sulfites: Ar—O—S(O)O$^-$ such as benzene sulfite and toluene sulfite; xi) alkyl sulfates: Alk-O—S(O)$_2$O$^-$ such as methyl sulfate and ethyl sulfate; xii) aryl sulfates: Ar—O—S(O)$_2$O$^-$; xiii) phosphate; xiv) acetate; xv) triflate; and xvi) borates such as tetrafluoroborate.

More particularly, An$^-$ which represents an anionic counterion or a mixture of anionic counterions, is chosen from halides such as chloride, bromide, fluoride or iodide; hydroxide; sulfate; a hydrogen sulfate; a linear or branched $C_1$-$C_6$ alkylsulfate, such as the methylsulfate or ethylsulfate ion; carbonates and hydrogen carbonates; carboxylic acid salts such as formate, acetate, citrate, tartrate, oxalate; linear or branched $C_1$-$C_6$ alkylsulfonates, such as the methylsulfonate ion; arylsulfonates for which the aryl part, preferably phenyl, is optionally substituted with one or more $C_1$-$C_4$ alkyl radicals, for instance 4-toluylsulfonate; alkylsulfonyls such as mesylate.

The compounds of formula (I) may also be in the form of solvates, for example a hydrate or a solvate of a linear or branched alcohol such as ethanol or isopropanol.

In the context of the invention, the term "derivative of formula (I)" is understood to mean all mesomeric, tautomeric or optical isomeric forms.

Preferably, the cationic 7-amino-1,2,3,4-tetrahydroquinoline derivatives of general formula (I) used for dyeing keratin fibres are chosen from the following compounds:

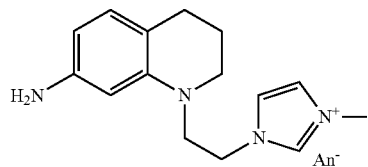

Salt of 1-[2-(7-amino-3,4-dihydroquinolin-1(2H)-yl)ethyl]-3-methyl-1H-imidazol-3-ium, An$^-$

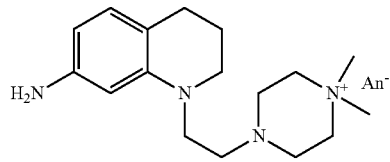

Salt of 4-[2-(7-amino-3,4-dihydroquinolin-1(2H)-yl)ethyl]-1,1-dimethylpiperazin-1-ium, An$^-$

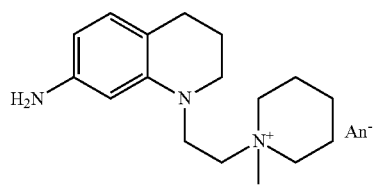

Salt of 1-[2-(7-amino-3,4-dihydroquinolin-1(2H)-yl)ethyl]-1-methylpiperidinium, An$^-$

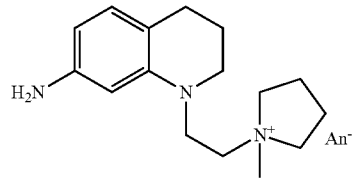

Salt of 1-[2-(7-amino-3,4-dihydroquinolin-1(2H)-yl)ethyl]-1-methylpyrrolidinium, An$^-$

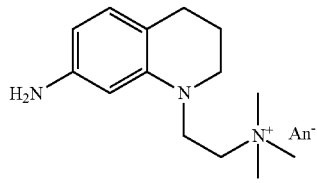

Salt of 2-(7-amino-3,4-dihydroquinolin-1(2H)-yl)-N,N,N-trimethylethanaminium, An$^-$

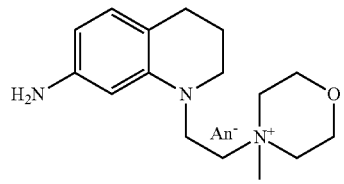

Salt of 4-[2-(7-amino-3,4-dihydroquinolin-1(2H)-yl)ethyl]-4-methylmorpholin-4-ium, An$^-$

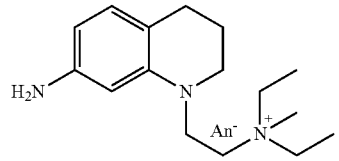

Salt of 2-(7-amino-3,4-dihydroquinolin-1(2H)-yl)-N,N,-diethyl-N-methylethanaminium, An$^-$

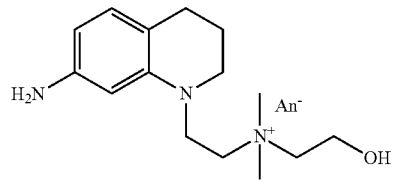

Salt of 2-(7-amino-3,4-dihydroquinolin-1(2H)-yl)-N-(2-hydroxyethyl)-N,N-dimethylethanaminium, An$^-$

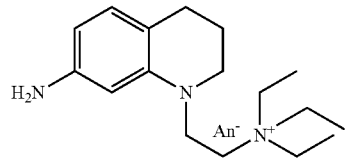

Salt of 2-(7-amino-3,4-dihydroquinolin-1(2H)-yl)-N,N,N-triethylethanaminium, An$^-$

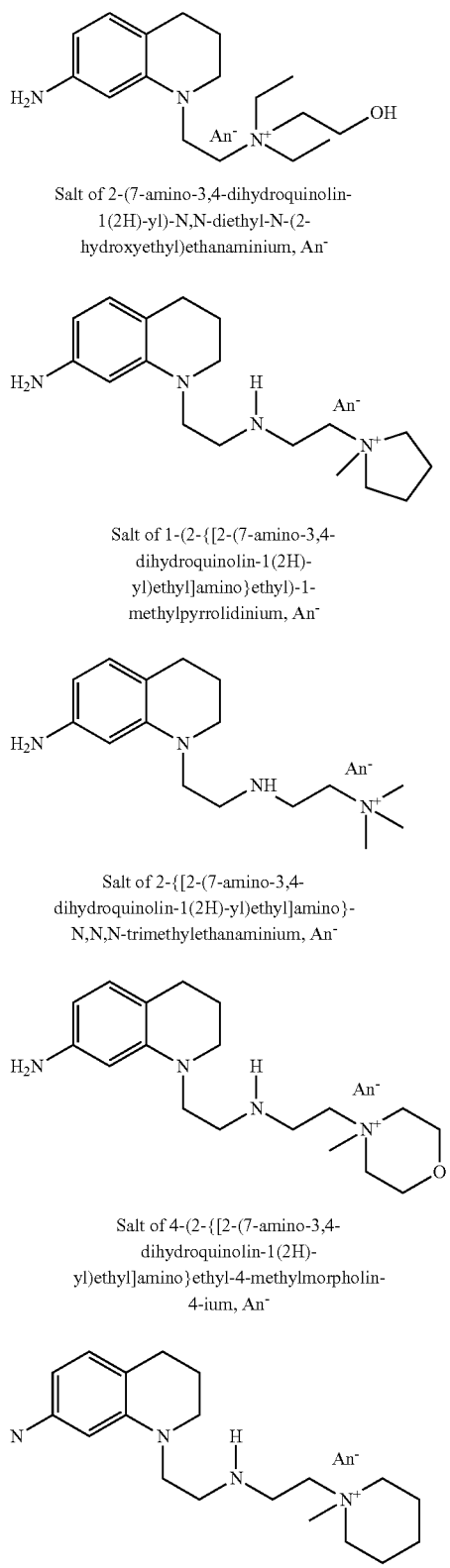
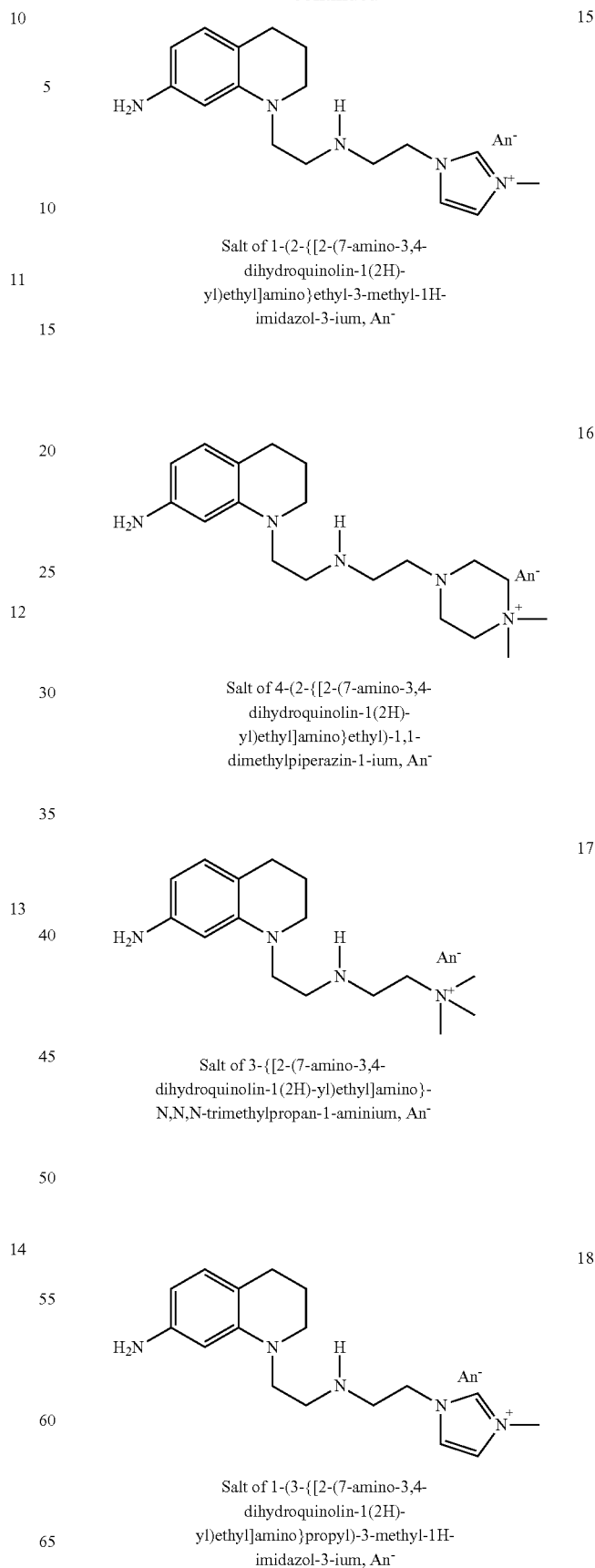

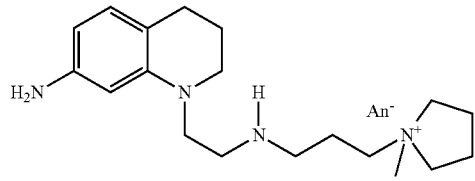

Salt of 1-(3-{[2-(7-amino-3,4-dihydroquinolin-1(2H)-yl)ethyl]amino}propyl)-1-methylpyrrolidinium, An⁻

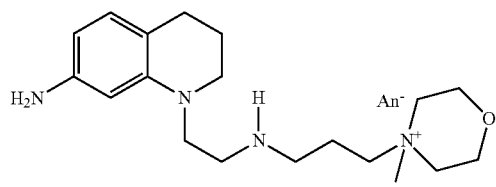

Salt of 4-(3-{[2-(7-amino-3,4-dihydroquinolin-1(2H)-yl)ethyl]amino}propyl)-4-methylmorpholin-4-ium, An⁻

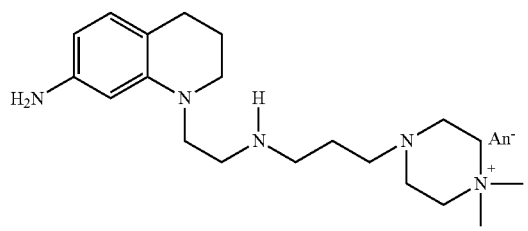

Salt of 4-(3-{[2-(7-amino-3,4-dihydroquinolin-1(2H)-yl)ethyl]amino}propyl)-1,1-dimethylpiperazin-1-ium, An⁻

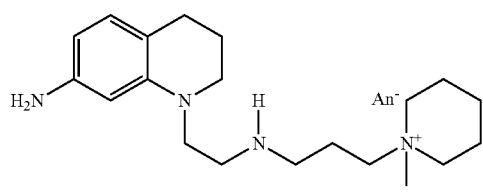

Salt of 1-(3-{[2-(7-amino-3,4-dihydroquinolin-1(2H)-yl)ethyl]amino}propyl)-1-methylpiperidinium, An⁻

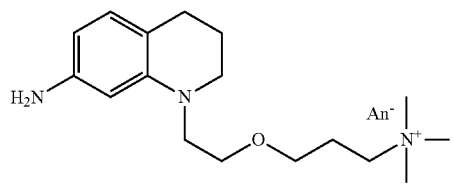

Salt of -3-[2-(7-amino-3,4-dihydroquinolin-1(2H)-yl)ethoxy]-N,N,N-trimethylpropan-1-aminium, An⁻

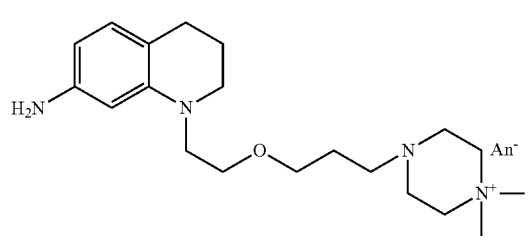

Salt of 4-{3-[2-(7-amino-3,4-dihydroquinolin-1(2H)-yl)ethoxy]propyl}-1,1-dimethylpiperazin-1-ium, An⁻

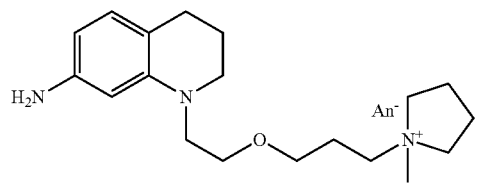

Salt of 11-{3-[2-(7-amino-3,4-dihydroquinolin-1(2H)-yl)ethoxy]propyl}-1-methylpyrrolidinium, An⁻

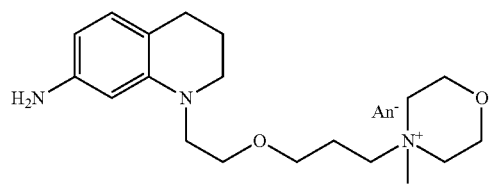

Salt of 4-{3-[2-(7-amino-3,4-dihydroquinolin-1(2H)-yl)ethoxy]propyl}-4-methylmorpholin-4-ium, An⁻

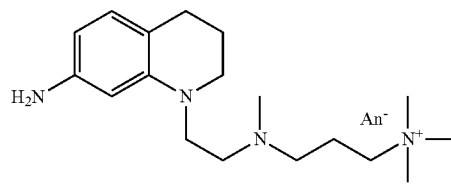

Salt of 3-{[2-(7-amino-3,4-dihydroquinolin-1(2H)-yl)ethyl](methyl)amino}-N,N,N-trimethylpropan-1-aminium, An⁻

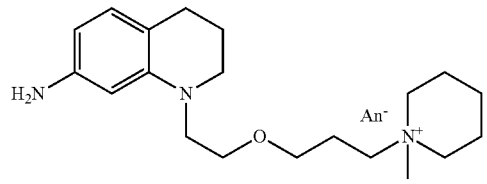

Salt of 1-{3-[2-(7-amino-3,4-dihydroquinolin-1(2H)-yl)ethoxy]propyl}-1-methylpiperidinium, An⁻

-continued

29

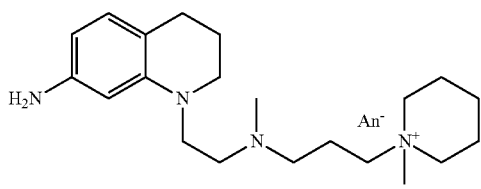

Salt of 1-(3-{[2-(7-amino-3,4-
dihydroquinolin-1(2H)-yl)-2-
oxoethyl](methyl)amino}propyl)-1-
methylpiperidinium, An⁻

30

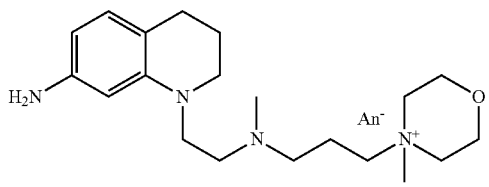

Salt of 4-(3-{[2-(7-amino-3,4-
dihydroquinolin-1(2H)-
yl)ethyl](methyl)amino}propyl)-4-
methylmorpholin-4-ium, An⁻

31

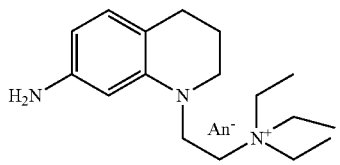

Salt of 2-(7-amino-3,4-dihydroquinolin-
1(2H)-yl)-N,N,N-triethylethanaminium,
An⁻

32

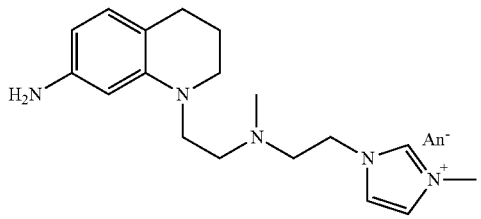

Salt of 1-(2-{[2-(7-amino-3,4-
dihydroquinolin-1(2H)-2-
oxoethyl(methyl)amino}ethyl)-3-methyl-
1H-imidazol-3-ium, An⁻

33

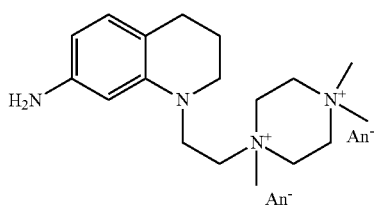

Salt of 1-[2-(7-amino-3,4-
dihydroquinolin-1(2H)yl)ethyl]-1,4,4-
trimethylpiperazinediium, An⁻ with An⁻, which may be identical or different, representing an anionic counterion as defined previously;
compounds 1 to 33 and also the salts thereof with organic or inorganic acids or bases, and/or the solvates thereof.

According to one particular embodiment, the synthesis of the compounds of formula (I) can be carried out according to the following scheme (1), (2) or (3): the first step consisting of a conventional reaction of N-substitution of 7-nitro-1,2,3,4-tetrahydroquinoline (1) by reaction:
 either with the cationic reactant Y'-L-CAT⁺, An⁻ with An⁻, Y', L, and CAT⁺ as defined hereinafter, so as to give the reaction intermediate (2) (scheme (1), pathway i));
 or with the non-cationic reactant Precat-L-Y' with Precat, Y', and L as defined hereinafter, so as to give the reaction intermediate (3) (scheme (1), pathway iii));
 or with the non-cationic reactant X'-L-Y' with X', Y' and L as defined hereinafter, so as to give the reaction intermediate (5) (scheme (1), pathway vii));
 or more specifically the first step is a reaction of N-substitution of 7-nitro-1,2,3,4-tetrahydroquinoline (1)
  by "alkylation" using reactant (A) X'—C($R_8$)($R_9$)—CH$_2$—Y, with $R_8$ and $R_9$ as defined previously, X' and Y, which may be identical or different, preferably different, representing a leaving or nucleofuge group such as a halogen atom, for instance chlorine, bromine or iodine, or a protected hydroxyl group such as mesylate, tosylate or triflate, preferably tosylate (scheme (2), pathway i)) so as to give the intermediate (6);
 or else
  by "acylation" using reactant (B) Y—C(W)—C($R_8$)($R_9$)—X', with $R_8$, $R_9$, X' and Y as defined previously, W representing an oxygen or sulfur atom or an NR group with R representing a hydrogen atom or a linear or branched ($C_1$-$C_6$)alkyl group, preferably W=oxygen, (scheme (3), pathway i)) so as to give the intermediate (6');

the intermediates (5), (6) and (6') comprising a nucleofuge group X' can subsequently:
 either undergo nucleophilic substitution by the non-cationic reactant Precat-H or the anionic reactant Precat⁻, M⁺, such as Het-H; Het⁻, M⁺; $R_7R_8$NH or $R_7R_8$N⁻, M⁺ with Het representing a heterocyclic group, $R_7$ and $R_8$ as defined hereinafter, M⁺ representing an alkali metal or alkaline-earth metal, such as Na, K or Li, and Precat, L' and X as defined previously, so as to give the intermediates (8) and (8') respectively (schemes (2) and (3), pathway iii));
 or undergo nucleophilic substitution by the cationic reactant An⁻, CAT⁺-[L'-X]$_n$—H or the zwitterionic reactant CAT⁺-[L'-X]$_n$⁻, such as the alkoxide CAT⁺-L'-O⁻, with CAT⁺, An⁻, L' and X as defined previously, so as to give the intermediates (7) and (7') respectively (schemes (2) and (3), pathway ii));
 or undergo nucleophilic substitution by the cationic reactant An⁻, CAT⁺-[L'-X]$_n$—H or the zwitterionic reactant CAT⁺-[L'-X]$_n$⁻, such as the alkoxide CAT⁺-L'-O⁻, with CAT⁺, An⁻, L' and X as defined previously, so as to give the intermediates (7) and (7') respectively (schemes (2) and (3), pathway ii));
 or undergo nucleophilic substitution by the non-cationic reactant Precat-[L'-X]$_n$—H or the anionic reactant Precat-[L'-X]$_n$⁻, M⁺ such as the alkoxide Precat-L'-O⁻, M⁺, with M⁺ representing an alkali metal or an alkaline-earth metal, such as Na, K or Li, and Precat, L' and X as defined previously, so as to give the intermediates (8) and (8') respectively (schemes (2) and (3), pathway iii));

the intermediates (7') and (8') can then be reduced by conventional reduction, preferably by hydroboration, for instance with $BH_3$, so as to give the compounds (7) and (8) respectively (scheme (3), pathway viii) and pathway v));

the compounds (2), (3), (7) and (8) can be subsequently reduced (scheme (1), pathways ii) and v); scheme (2), pathways v) and vi); scheme (3), pathways vi) and ix)), by conventional reduction, preferably catalytic reduction, so as to give the compounds of formula (I), (4), (9) or (II), the latter belonging to the compounds of formula (I);

the compounds (3), (4), (8) or (9) can be subsequently cationized, preferably by alkylation of a heteroatom of the heterocycle, or of the amino group $R_7R_8N$— with a reactant of the type $R'_9$—X' with X' as defined previously for Y', and $R'_9$ representing a linear or branched $(C_1-C_6)$alkyl group, which is optionally substituted, preferably with one or more hydroxyl groups (scheme (1), pathways iv) and vi) and schemes (2) and (3), pathways iv) and vii)) so as to give the compounds of formula (2), (I), (7), (7') or (II), the latter belonging to the compounds of formula (I);

Precat represents a cationizable group, i.e. is a cationizable radical which gives the radical $CAT^+$ after cationization; in particular, Precat is chosen from:
a monocyclic or polycyclic, saturated or unsaturated, aromatic or nonaromatic, heterocyclic radical, optionally substituted preferably with one or more radicals, which may be identical or different, preferably chosen from linear or branched $C_1$-$C_4$ alkyl radicals or $C_1$-$C_4$ hydroxyalkyl radicals;
an amino radical $R_7R_8N$—, with $R_7$ and $R_8$, which may be identical or different, representing a linear or branched $(C_1-C_6)$alkyl group, which is optionally substituted, preferably with one or more hydroxyl groups;

Precat is preferably cationized by alkylation of a heteroatom of the heterocycle, or of the amino group

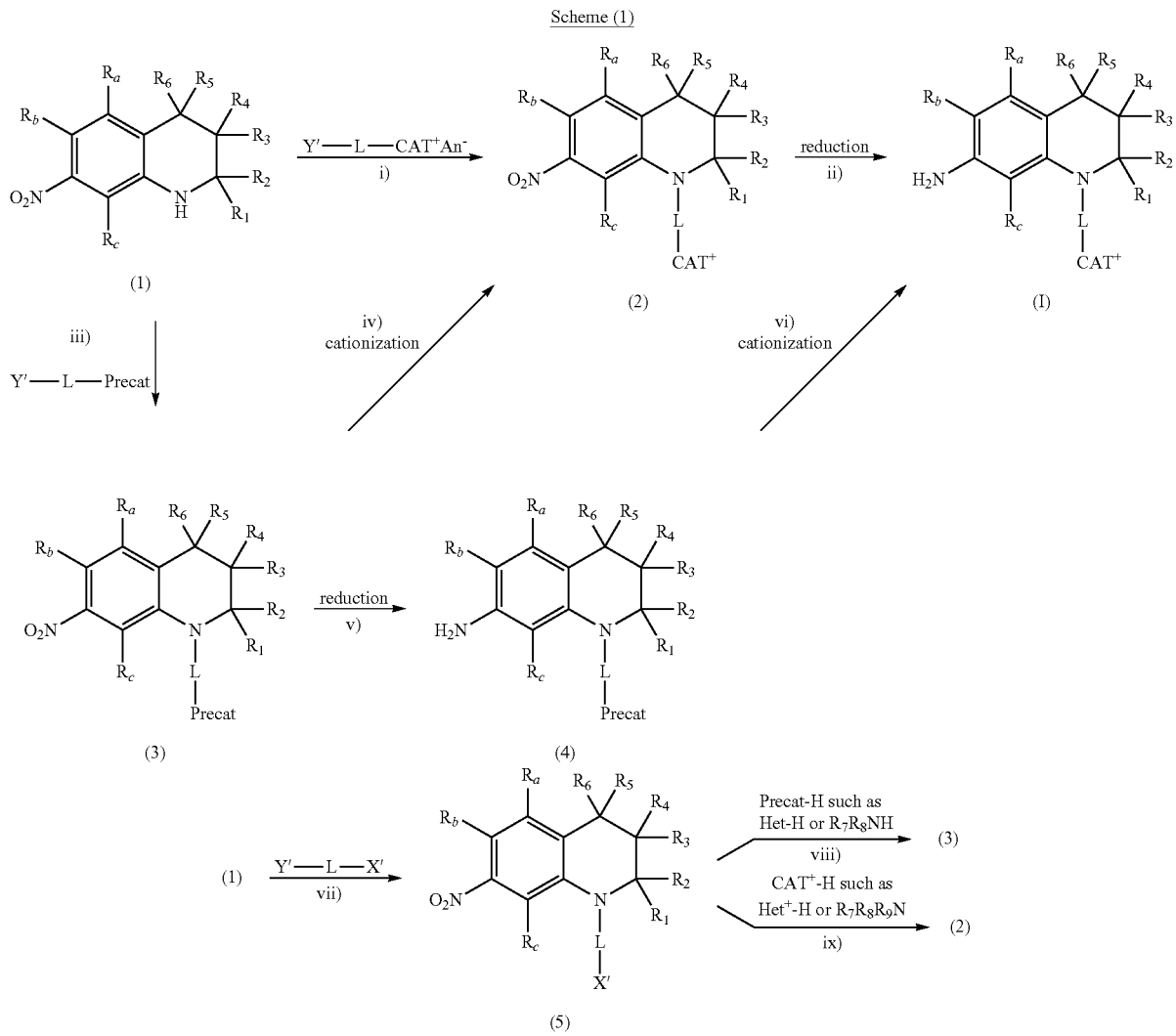

in which formula (I) as defined previously and formulae (1), (2), (3) and (4):
$CAT^+$, $An^-$, L, $R_a$, $R_b$, $R_c$, $R_1$, $R_2$, $R_3$, $R_4$, $R_5$, $R_6$, $R_7$, $R_8$ and $R_9$ are as defined previously;
Y' represents a nucleofuge group, such as a halogen, in particular chlorine, bromine or iodine, or a protected hydroxyl group, such as mesylate, tosylate, or triflate;

$R_7R_8N$— with a reactant of the type R'—X' with X' as previously defined for Y', and $R'_9$ representing a linear or branched $(C_1-C_6)$alkyl group, which is optionally substituted, preferably with one or more hydroxyl groups;
Het-H represents a heterocyclic group as defined previously comprising at least one N—H group;

Het$^+$-H represents a cationic heterocyclic group as defined previously.
The compounds of formula (II) can be synthesized according to the following schemes (2) and (3):
Scheme (2)
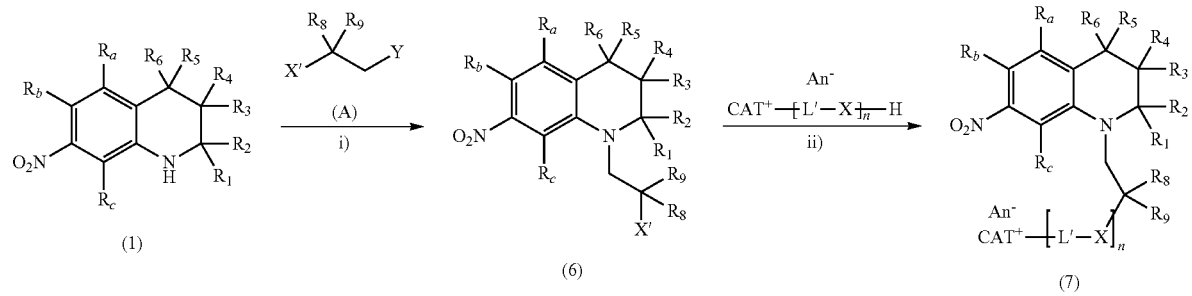
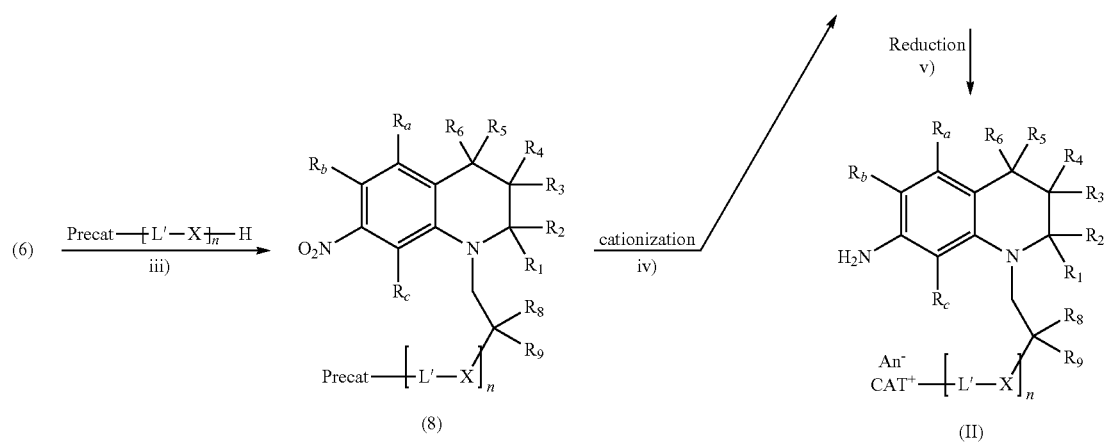
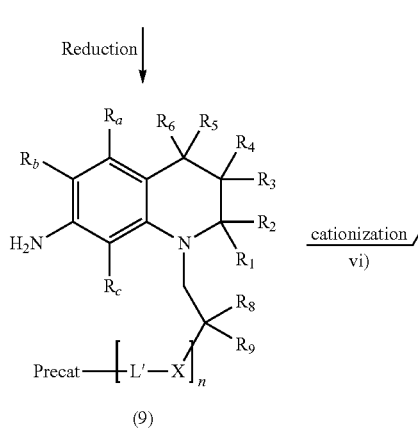
X' is a nucleofuge group such as a halogen
Y is a nucleofuge group such as a halogen, preferably different from X', or a hydroxyl group protected, for example, with a tosylate Scheme (3)

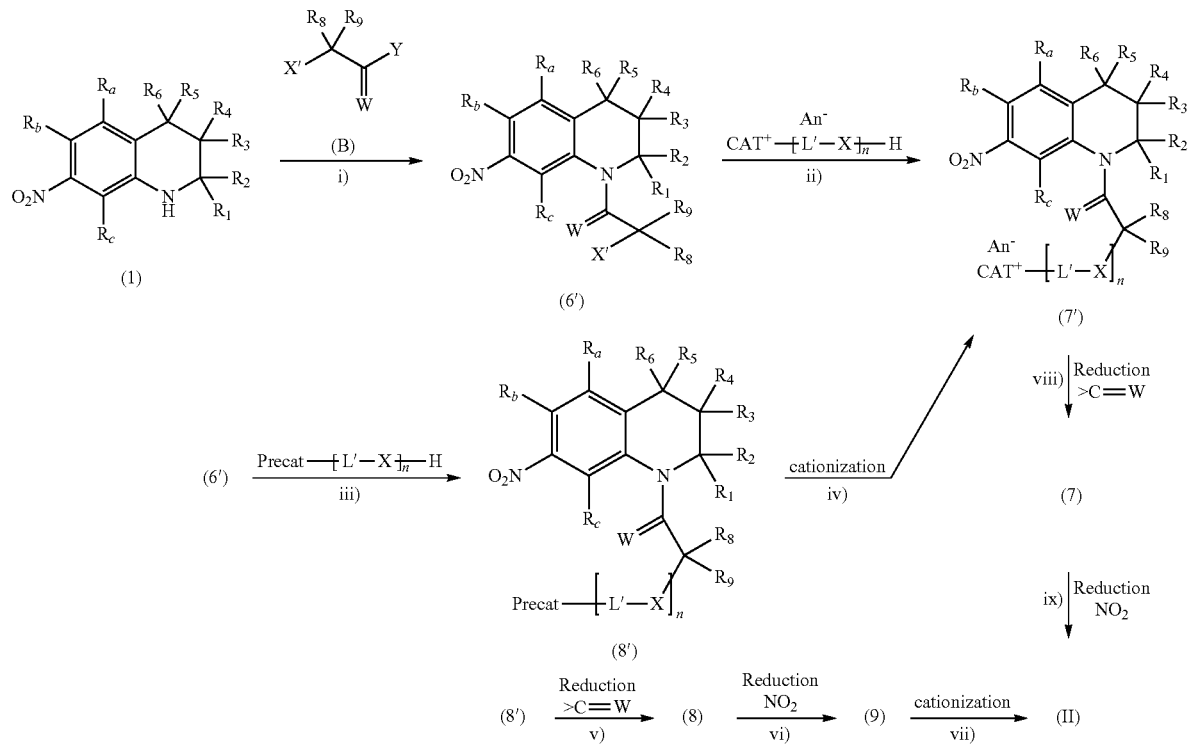

X' is a nucleofuge group such as a halogen
Y is a nucleofuge group such as a halogen, preferably different from X',
or a hydroxyl group protected, for example, with a tosylate
W is O, S, NR with R representing H or $(C_1\text{---}C_6)$alkyl in which schemes (2) and (3), formulae (II) and (1) are as defined previously and, in formulae (6), (6'), (7), (7'), (8), (8'), and (9):

$CAT^+$, $An^-$, Precat, $R_a$, $R_b$, $R_c$, $R_1$, $R_2$, $R_3$, $R_4$, $R_5$, $R_6$, $R_7$, $R_8$ and $R_9$ are as defined previously;

n, L' and X are as defined previously;

X' and Y, which may be identical or different, represent a nucleofuge group, such as a halogen, in particular chlorine, bromine or iodine, or a protected hydroxyl group, such as mesylate, tosylate, or triflate; and W represents an oxygen or sulfur atom, or an imino group NR with R representing a hydrogen atom or a linear or branched $(C_1\text{-}C_6)$alkyl group.

In particular, the first step is an acylation reaction or an alkylation reaction of the 7-nitro-1,2,3,4-tetrahydroquinoline (1) under conventional conditions, for example by reaction with a haloacetyl halide or a derivative (A) in a polar solvent of alcohol, alkyl acetate, THF, dioxane, etc., type, at a temperature of between 0° C. and 100° C. Depending on the nature of the haloacetyl, the compounds (7) or (10) are obtained, the reaction with the compound (A) giving the intermediate (2).

The steps of reduction of the carbonyl, thiocarbonyl, or iminocarbonyl >C=W function of schemes (1), (2) and (3) are carried out under conventional conditions known to those skilled in the art; mention may be made of, for example, by hydroboration such as with $BH_3$ in a polar or non-polar solvent, for instance THF, glyme, dioxane or diethyl ether.

The reduction of the nitro group in reaction schemes (1) to (3) is carried out under conventional conditions known to those skilled in the art, preferably by catalytic reduction, for example by performing a hydrogenation reaction by heterogeneous catalysis in the presence of Pd/C, Pd(II)/C, Ni/Ra, etc., or alternatively by performing a reduction reaction with a metal, for example with zinc, iron, tin, etc. (see *Advanced Organic Chemistry*, 3rd Edition, J. March, 1985, Wiley Interscience and *Reduction in Organic Chemistry*, M. Hudlicky, 1983, Ellis Horwood Series Chemical Science).

The cationization is carried out by reaction with at least one equivalent of alkyl halide or sulfate, such as methyl sulfate, or alkyl carbonate in an aprotic polar solvent such as THF or acetonitrile or dioxane or ethyl acetate, preferably for 15 minutes to 24 h, at a temperature ranging from 15° C. to the reflux temperature of the solvent, so as to give the cationic nitrogenous compounds.

A subject of the invention is also the nitrogenous reaction intermediates of formulae (2), (7), and (7') as defined in schemes (1) to (3) above, with $R_a$ to $R_c$, $R_1$ to $R_6$, W, n, $CAT^+$, $An^-$, L, L', and X as previously defined.

Composition

The present application also relates to a cosmetic dyeing composition, in particular for dyeing keratin fibres such as the hair, comprising, in a medium appropriate for dyeing, at least one cationic 7-amino-1,2,3,4-tetrahydroquinoline derivative of general formula (I), as defined previously.

Preferably, the concentration of cationic 7-amino-1,2,3,4-tetrahydroquinoline derivative of general formula (I) ranges from 0.0001% to 20%, preferably from 0.005% to 6% by weight, relative to the total weight of the composition.

The medium appropriate for dyeing generally comprises water or a mixture of water and at least one organic solvent such as, for example, branched or unbranched $C_1$-$C_4$ lower alcohols, such as ethanol and isopropanol; polyols and polyol ethers, such as 2-butoxyethanol, propylene glycol, propylene glycol monomethyl ether, diethylene glycol monoethyl ether and monomethyl ether, and glycerol, and also aromatic alcohols such as benzyl alcohol or phenoxyethanol, and mixtures thereof.

Advantageously the cosmetic composition comprises at least one cosmetic adjuvant chosen from the group made up of antioxidants, penetrants, sequestrants, fragrances, buffers, dispersants, surfactants, conditioning agents, filmi-forming agents, polymers, ceramides, preservatives, nacres or opacifiers, vitamins or provitamins.

The above adjuvants are generally present in an amount, for each of them, ranging from 0.01% to 20% by weight, relative to the weight of the composition.

The composition also comprises at least one oxidation base. These bases may in particular be chosen from para-phenylenediamines, bis-phenylalkylenediamines, para-aminophenols, ortho-aminophenols and heterocyclic bases, and the addition salts thereof.

Among the para-phenylenediamines, mention may more particularly be made, by way of example, of para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl 3-methylaniline, N,N-bis-(β-hydroxyethyl)-para-phenylenediamine, 4-N,N-bis-(β-hydroxyethyl) amino-2-methylaniline, 4-N,N-bis-(β-hydroxyethyl)amino-2-chloroaniline, 2-3-hydroxyethyl-para-phenylenediamine, 2-fluoro-para-phenylenediamine, 2-isopropyl para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β hydroxyethylamino-5-aminotoluene, 3-hydroxy-1-(4'-aminophenyl)pyrrolidine, 6-(4-aminophenylamino)hexan-1-ol, N-(4-amino-3-methylphenyl)-N-[3-(1H-imidazol-1-yl)propyl]amine, N-(4-aminophenyl)-N-[3-(1H-imidazol-1-yl)propyl]amine and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis-(β-hydroxyethyl)-para-phenylenediamine, 2-chloro-para-phenylenediamine, 2-β-acetylaminoethyloxy-para-phenylenediamine, 2-[{2-[(4-aminophenyl)amino]ethyl}(2-hydroxyethyl)amino]ethanol and the addition salts thereof with an acid are particularly preferred.

Among the bisphenylalkylenediamines, mention may be made, by way of example, of N,N'-bis(β-hydroxyethyl)-N, N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof with an acid.

Among the para-aminophenols mention may be made, by way of example, of para-aminophenol, 4-amino-3-methylphenol, 4-amino-3-fluorophenol, 4-amino-2-chlorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, 4-amino-2,6-dichlorophenol, 4-amino-6-[((5'-amino-2'-hydroxy-3'-methyl)phenyl)methyl]-2-methylphenol, bis[(5'-amino-2'-hydroxy)phenyl-methane and the addition salts thereof with an acid.

Among the ortho-aminophenols, mention may be made, by way of example, of 2-aminophenol, 2-amino-5-methylphenol, 2-amino-6-methylphenol and 5-acetamido-2-aminophenol, and the addition salts thereof with an acid.

Among the heterocyclic bases, mention may be made, by way of example, of pyridine derivatives, pyrimidine derivatives and pyrazole derivatives.

Among the pyridine derivatives, mention may be made of the compounds described, for example, in patents GB 1 026 978 and GB 1 153 196, such as 2,5-diaminopyridine, 2-(4-methoxyphenyl)amino-3-aminopyridine, 3,4-diaminopyridine, and the addition salts thereof with an acid.

Other pyridine oxidation bases of use in the present invention are the 3-aminopyrazolo[1,5-a]pyridine oxidation bases or the addition salts thereof described, for example, in patent application FR 2 801 308. Mention may be made, by way of example, of pyrazolo[1,5-a]pyrid-3-ylamine, 2-(acetylamino)pyrazolo[1,5-a]pyrid-3-ylamine, 2-(morpholin-4-yl) pyrazolo[1,5-a]pyrid-3-ylamine, 3-aminopyrazolo[1,5-a]pyridine-2-carboxylic acid, 2-methoxypyrazolo[1,5-a]pyrid-3-ylamino, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino] ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol and the addition salts thereof with an acid.

Among the pyridine bases that are of use in the present invention, mention may also be made of the compounds described in patent applications EP 1792903 and EP 1792606 and the addition salts thereof.

Mention may be made, among the pyrimidine derivatives, of the compounds described, for example, in patents DE 2359399, JP 88-169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof and the tautomeric forms thereof, when a tautomeric equilibrium exists.

Among the pyrazolopyrimidine derivatives, mention may be made of the compounds described, for example, in patent applications EP 0847271, EP 0926149 and EP 1147109 and the addition salts thereof.

Among the pyrazole derivatives that may be mentioned are the compounds described in patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof.

By way of oxidation bases, mention may also be made of the diamino-N,N-dihydropyrazolone derivatives of formula (III) or one of the addition salts or solvates thereof:

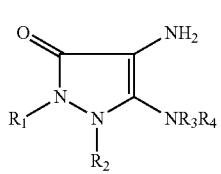

(III)

in which formula (III):
$R_1$, $R_2$, $R_3$ and $R_4$, which may be identical or different, represent:
a linear or branched $C_1$-$C_6$ alkyl radical optionally substituted with one or more radicals chosen from the group consisting of an —$OR_5$ radical, an —$NR_6R_7$ radical, a carboxy radical, a sulfonic radical, a carboxamido radical —C(O)—$NR_6R_7$, a sulfonamido radical —$S(O)_2$—$NR_6R_7$, a heteroaryl, an aryl optionally substituted with a ($C_1$-$C_4$)alkyl group, a hydroxyl, a $C_1$-$C_2$ alkoxy, an amino, or a (di)($C_1$-$C_2$)alkylamino;
an aryl radical optionally substituted with one or more ($C_1$-$C_4$)alkyl, hydroxyl, $C_1$-$C_2$ alkoxy, amino or (di)($C_1$-$C_2$)alkylamino;
a 5- or 6-membered heteroaryl radical, optionally substituted with one or more radicals chosen from ($C_1$-$C_4$)alkyl and ($C_1$-$C_2$)alkoxy;
$R_3$ and $R_4$ may also represent a hydrogen atom;
$R_5$, $R_6$ and $R_7$, which may be identical or different, represent a hydrogen atom; a linear or branched $C_1$-$C_4$ alkyl radical optionally substituted with one or more radicals chosen from the group consisting of a hydroxyl, a $C_1$-$C_2$ alkoxy, a carboxamido —C(O)—$NR_8R_9$, a sulfonyl —$S(O)_2$—$R_8$, an aryl optionally substituted with a ($C_1$-$C_4$)alkyl, a hydroxyl, a $C_1$-$C_2$ alkoxy, an amino, a (di)($C_1$-$C_2$)alkylamino; an aryl optionally substituted with a ($C_1$-$C_4$)alkyl, a hydroxyl, a $C_1$-$C_2$ alkoxy, an amino, or a (di)($C_1$-$C_2$)alkylamino;
$R_6$ and $R_7$, which may be identical or different, may also represent a carboxamido radical —C(O)—$NR_8R_9$; a sulfonyl —$S(O)_2$—$R_8$;
$R_8$ and $R_9$, which may be identical or different, represent a hydrogen atom; or a linear or branched $C_1$-$C_4$ alkyl radical which is optionally substituted with one or more of hydroxyl or $C_1$-$C_2$ alkoxy;
$R_1$ and $R_2$, on the one hand, and $R_3$ and $R_4$, on the other hand, may form, with the nitrogen atoms to which they are attached, a saturated or unsaturated heterocycle containing 5 to 7 members which is optionally substituted with one or more radicals chosen from the group consisting of halogen atoms, amino, (di)($C_1$-$C_4$)alkylamino, hydroxyl, carboxyl, carboxamido and ($C_1$-$C_2$) alkoxy radicals, and $C_1$-$C_4$ alkyl radicals optionally substituted with one or more hydroxyl, amino, (di)alkylamino, alkoxy, carboxyl or sulfonyl radicals;
$R_3$ and $R_4$ may also form, together with the nitrogen atom to which they are attached, a 5- or 7-membered heterocycle in which the carbon atoms may be replaced with an optionally substituted oxygen or nitrogen atom.

These diamino-N,N-dihydropyrazolone derivatives are described in particular in application FR 2866338, and one particularly preferred derivative is 2,3-diamino-6,7-dihydro-1H,5H-pyrazolo[1,2-a]pyrazol-1-one dimethanesulfonate.

Oxidation bases that may also be mentioned include the diamino-N,N-dihydropyrazolone derivatives of formula (IV) or one of the addition salts or solvates thereof:

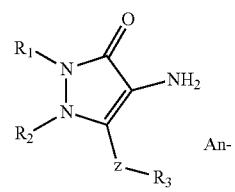

(IV)

in which formula (IV):
z represents independently:
a covalent single bond,
a divalent radical chosen from an oxygen atom and an —N($R_6$)— radical, with $R_6$ representing a hydrogen atom or a $C_1$-$C_6$ alkyl radical, or $R_6$ with $R_3$ together form, with the nitrogen atom which bears them, a substituted or unsubstituted, saturated or unsaturated and aromatic or nonaromatic 5- to 8-membered heterocycle, optionally containing one or more other heteroatoms or groups chosen from N, 0, S, —$S(O)_2$—, and —C(O)—, it being possible for the heterocycle to be cationic and/or substituted with a cationic radical,
a divalent radical —$N^+(R_7)(R_8)$— with $R_7$ and $R_8$ independently representing a $C_1$-$C_6$ alkyl radical; the alkyl radical may be substituted with an OH or an alkoxy: —O($C_1$-$C_6$)alkyl,
$R_3$ represents:
a hydrogen
a $C_1$-$C_{10}$ alkyl radical which is optionally substituted, it being possible for the alkyl radical to be interrupted with a heteroatom or a group chosen from O, N, Si, S, —S(O)— and —$S(O)_2$—,
a $C_1$-$C_{10}$ alkyl radical which is substituted and/or interrupted with a cationic radical,
a halogen,
an —$SO_3H$ radical,
a 5- to 8-membered ring which is substituted or unsubstituted, saturated, unsaturated or aromatic, optionally containing one or more heteroatoms or groups chosen from N, O, S, —S(O)$_2$— and —C(O)—, it being possible for the ring to be cationic and/or substituted with a cationic radical, $R_1$ and $R_2$, which may be identical or different, represent:
- a linear or branched $C_1$-$C_6$ alkyl radical optionally substituted with one or more radicals chosen from an $OR_5$ radical, an —$NR_9R_{10}$ radical, a carboxy radical, a sulfonic radical, a carboxamido radical —C(O)—$NR_9R_{10}$, a sulfonamido radical —S(O)$_2$—$NR_9R_{10}$, a heteroaryl, an aryl optionally substituted with a ($C_1$-$C_4$)alkyl group, a hydroxyl group, a $C_1$-$C_2$ alkoxy group, an amino group, or a (di)($C_1$-$C_2$)alkylamino group;
- an aryl radical optionally substituted with one or more ($C_1$-$C_4$)alkyl, hydroxyl, $C_1$-$C_2$ alkoxy, amino or (di)($C_1$-$C_2$)alkylamino;
- a 5- or 6-membered heteroaryl radical which is optionally substituted with one or more radicals chosen from ($C_1$-$C_4$)alkyl which is monosubstituted or polysubstituted with an OH or an —Oalkyl, or ($C_1$-$C_2$)alkoxy;
- $R_1$ and $R_2$ may form, with the nitrogen atoms to which they are attached, a saturated or unsaturated heterocycle containing 5 to 7 members which is optionally substituted with one or more radicals chosen from the group consisting of halogen atoms, amino, (di)($C_1$-$C_4$)alkylamino, hydroxyl, carboxyl, carboxamido and ($C_1$-$C_2$)alkoxy radicals, and $C_1$-$C_4$ alkyl radicals which are optionally substituted with one or more hydroxyl, amino, (di)alkylamino, alkoxy, carboxyl or sulfonyl radicals,
- An– represents an anion or a group of anions making it possible to ensure the electroneutrality of the compounds of formula (IV), on the condition that at least one of the groups Z and $R_3$ represents a cationic radical. These diamino-N,N-dihydropyrazolone derivatives are described in patent application FR 2 927 078.

In general the concentration of the oxidation base(s) ranges from 0.0001% to 20% and preferably from 0.005% to 6% by weight, relative to the total weight of the composition.

The composition according to the invention preferably contains at least one additional oxidation coupler other than the cationic 7-amino-1,2,3,4-tetrahydroquinoline derivatives of general formula (I).

Among these oxidation couplers mention may in particular be made of meta-phenylenediamines, meta-aminophenols, meta-diphenols, naphthalenic couplers and heterocyclic couplers, and the addition salts thereof.

By way of example, mention may be made of 2-methyl-5-aminophenol, 5-N-(β-hydroxyethyl)amino-2-methylphenol, 6-chloro-2-methyl-5-aminophenol, 3-aminophenol, 1,3-dihydroxybenzene (or resorcinol), 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis-(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino) toluene and the addition salts thereof.

In general, the concentration of the oxidation coupler(s) ranges from 0.0001% to 20% and preferably from 0.005% to 6% by weight, relative to the total weight of the composition.

In general, the addition salts with an acid that can be used for the oxidation bases and the couplers are chosen in particular from hydrochlorides, hydrobromides, sulfates, citrates, succinates, tartrates, lactates, tosylates, benzenesulfonates, phosphates and acetates.

The dyeing composition in accordance with the invention may further comprise one or more direct dyes, which may in particular be chosen from neutral, acidic or cationic nitrobenzene dyes, neutral, acidic or cationic azo direct dyes, neutral, acidic or cationic quinone, and especially anthraquinone, direct dyes, azine direct dyes, methine, azomethine, triarylmethane and indoamine direct dyes and natural direct dyes. The composition according to the invention preferably comprises at least one dye chosen from cationic direct dyes and natural direct dyes.

Among the cationic direct dyes that can be used according to the invention, mention may be made of the cationic azo direct dyes described in patent applications WO 95/15144, WO 95/01772 and EP-714954.

Among these compounds, mention may be made very particularly of the following dyes:
1,3-dimethyl-2-[[4-(dimethylamino)phenyl]azo]-1H-imidazolium halide (chloride),
1,3-dimethyl-2-[(4-aminophenyl)azo]-1H-imidazolium halide (chloride),
1-methyl-4-[(methylphenylhydrazono)methyl]pyridinium salt (methyl sulfate).

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes and in particular henna-based extracts or poultices may also be used.

The direct dye(s) preferably represent(s) approximately from 0.001% to 20% by weight of the total weight of the composition, and even more preferentially approximately from 0.005% to 10% by weight.

Those skilled in the art will of course ensure that the adjuvant(s), additional oxidation dye precursors and direct dyes are chosen such that the advantageous properties intrinsically attached to the oxidation dyeing composition in accordance with the invention are not, or not substantially, adversely affected by the intended addition(s).

The pH of the dye composition in accordance with the invention is generally between approximately 3 and 12 and preferably between approximately 5 and 11. It may be adjusted to the desired value by means of acidifying or alkalinizing agents customarily used in the dyeing of keratin fibres, or alternatively using standard buffer systems.

Among the acidifying agents, mention may be made of those already mentioned for salifying the compounds of formula (I) to give a salt with an organic or inorganic acid, by way of example, inorganic or organic acids other than dicarboxylic acids, such as hydrochloric acid, ortho-phosphoric acid, sulfuric acid, carboxylic acids such as acetic acid, tartaric acid, citric acid or lactic acid, and sulfonic acids.

Among the alkalinizing agents, mention may be made of those already mentioned for salifying the compounds of formula (I) to give a salt with an organic or inorganic base, by way of example, aqueous ammonia, alkali metal carbonates, alkanolamines, such as mono-, di- and triethanolamines, and derivatives thereof, sodium hydroxide, potassium hydroxide and the compounds of formula (V):

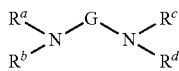 (V)

in which formula (V):
G is a linear or branched ($C_1$-$C_6$)alkylene group, optionally interrupted with one or more heteroatoms such as O or N, and/or optionally substituted with a hydroxyl group; in particular, G represents a propylene group;
$R^a$, $R^b$, $R^c$ and $R^d$, which may be identical or different, represent a hydrogen atom or a $C_1$-$C_4$ alkyl or hydroxy ($C_1$-$C_4$)alkyl radical.

The cosmetic composition according to the invention may be present in a variety of forms, such as in the form of liquids, creams, gels, or any other form which is appropriate for carrying out dyeing of keratin fibres, and in particular of human hair.

A subject of the present application is also a process for dyeing keratin fibres, in which the composition is applied to said fibres for a time sufficient to develop the desired colouration in the presence of an oxidizing agent, the oxidizing agent being applied before, simultaneously with or after the composition.

The colour may be developed at acidic, neutral or alkaline pH, and the oxidizing agent may be added to the composition of the invention just at the time of use, or it may be used starting from an oxidizing composition which comprises it and which is applied simultaneously with or sequentially to the composition of the invention.

In one particular embodiment the composition according to the present invention is mixed, preferably at the time of use, into a composition containing, in a medium appropriate for dyeing, at least one oxidizing agent, this oxidizing agent being present in an amount sufficient to develop a colouration.

In this particular embodiment, a ready-to-use composition is available which is a mixture of a composition according to the invention with at least one oxidizing agent. The resulting mixture is subsequently applied to the keratin fibres for a time sufficient for the desired colouration to develop. After a leave-in time of approximately 3 to 50 minutes, preferably approximately 5 to 30 minutes, the keratin fibres are rinsed, washed with shampoo, rinsed again and then dried.

The oxidizing agents conventionally used for the oxidation dyeing of keratin fibres are, for example, hydrogen peroxide, urea peroxide, alkali metal bromates, persalts such as perborates and persulfates, peracids and oxidase enzymes, among which mention may be made of peroxidases, 2-electron oxidoreductases such as uricases, and 4-electron oxygenases, for instance laccases. Hydrogen peroxide is particularly preferred.

The oxidizing composition may also contain various adjuvants conventionally used in compositions for dyeing the hair and as defined previously.

The pH of the oxidizing composition containing the oxidizing agent is such that, after mixing with the dyeing composition, the pH of the resulting composition applied to the keratin fibres preferably ranges between 3 and 12 approximately and even more preferentially between 5 and 11. It may be adjusted to the desired value by means of acidifying or alkalinizing agents customarily used in the dyeing of keratin fibres and as defined above.

The ready-to-use composition which is ultimately applied to the keratin fibres may be in a variety of forms, such as in the form of liquids, creams or gels or any other form appropriate for carrying out dyeing of keratin fibres, and in particular of human hair.

The present application further provides a method of dyeing keratin fibres, in which the ready-to-use composition is applied to said fibres for a time sufficient to develop the desired colouration.

The time sufficient to develop the desired colouration corresponds in general to a leave-in time of approximately 3 to 50 minutes, preferably approximately 5 to 30 minutes.

The invention further provides a dyeing kit or multi-compartment device in which a first compartment contains the dyeing composition defined above and a second compartment contains an oxidizing composition. This device may be equipped with a means allowing the desired mixture to be delivered to the hair, such as the devices described in patent FR-2 586 913 in the name of the Applicant.

Using this device, it is possible to dye the keratin fibres on the basis of a process which comprises mixing a dyeing composition in accordance with the invention with an oxidizing agent as defined previously, and applying the resulting mixture to the keratin fibres for a time sufficient to develop the desired colouration.

The evaluation of the coloration can be done visually or read on a spectrocolorimeter (such as Minolta CM3600d, illuminant D65, angle 10°, SCI values) for the L*, a*, b* colorimetric measurements. In this L*, a*, b* system, L* represents the intensity of the color, a* indicates the green/red color axis and b* indicates the blue/yellow color axis.

The lower the value of L, the darker or more intense the color.

The higher the value of a*, the redder the shade; the higher the value of b*, the yellower the shade.

The variation in coloring between the colored locks of natural white hair which is untreated (control) and after treatment or coloration are defined by ΔE*, corresponding to the colour uptake on keratin fibers, according to the following equation:

$$\Delta E^* = \sqrt{(L^* - L_o^*)^2 + (a^* - a_o^*)^2 + (b^* - b_o^*)^2}$$

In this equation, L*, a* and b* represent the values measured after dyeing the natural hair comprising 90% of white hairs and $L_o^*$, $a_o^*$ and $b_o^*$ represent the values measured for the untreated natural hair comprising 90% of white hairs.

The greater the value of ΔE, the greater the difference in color between the control locks and the dyed locks and the greater colour uptake is.

Chromaticity in the CIE L*, a*, b* colorimetric system is calculated according to the following equation:

$$C^* = \sqrt{a^{*2} + b^{*2}}$$

The greater the value of C*, the greater the chromaticity is.

The examples that follow serve to illustrate the invention without, however, being limiting in nature.

EXAMPLES a) Synthesis of 1-(chloroacetyl)-7-nitro-1,2,3,4-tetrahydroquinoline

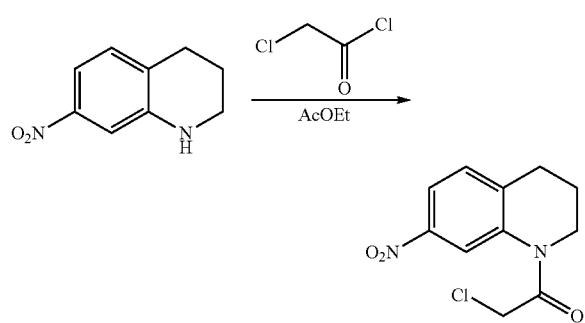

1.78 g of 7-nitro-1,2,3,4-tetrahydroquinoline (0.01 mol) are dissolved in 15 ml of ethyl acetate. This solution is run into a mixture of 15 ml of ethyl acetate and 0.80 ml of chloroacetyl chloride. A white precipitate forms immediately, and stirring is continued at 30° C. for 2 h (the reaction is monitored by thin layer chromatography (90/10 ethyl acetate/heptane)). After 2 h, since the reaction is incomplete, 0.2 equivalent of chloroacetyl chloride is added and the temperature is raised to 60° C.; the solid formed undergoes dissolution. When the reaction has finished, the mixture is cooled and the solvent is evaporated off. 2.46 g of a beige product which corresponds to the expected compound are recovered.

The spectroscopic and spectrometric data are in agreement with the structure of the expected compound.

Example 1

2-(7-amino-3,4-dihydroquinolin-1(2H)-yl)-N,N,N-trimethylethanammonium chloride hydrochloride

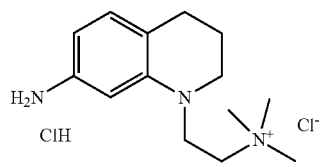 [SMILES: C[N+](C)(C)CCN1CCCc2ccc(N)cc21 ; Cl ; [Cl-]]

b) Synthesis of 2-(dimethylamino)-1-(7-nitro-3,4-dihydroquinolin-1 (2H)-yl)ethanone

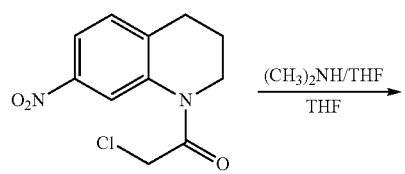

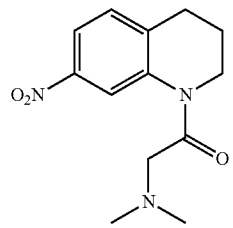

2-chloro-1-(7-nitro-3,4-dihydroquinolin-1(2H)-yl)ethanone (1 g, 3.9 mmol) was dissolved in 10 ml of dry THF and 7.8 ml of a 1M solution of dimethylamine in THF (7.8 mmol) were added. This reaction mixture was stirred at ambient temperature for 24 h. The solvent was removed under reduced pressure and the residue was crystallized from diethyl ether to give the expected compound 2-(dimethylamino)-1-(7-nitro-3,4-dihydroquinolin-1(2H)-yl)ethanone in the form of a brown solid (m.p. 130-132° C.).

The spectroscopic and spectrometric data are in accordance with the structure of the expected compound.

c) Synthesis of N,N-dimethyl-2-(7-nitro-3,4-dihydroquinolin-1(2H)-yl)ethanamine

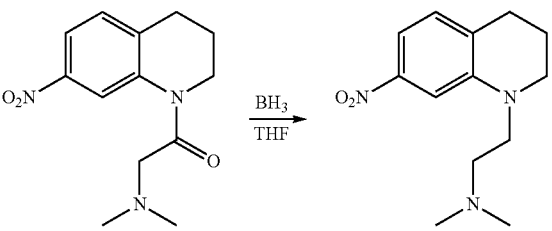

Under a nitrogen atmosphere, 1.2 g (4.6 mmol) of 2-(dimethylamino)-1-(7-nitro-3,4-dihydroquinolin-1(2H)-yl)ethanone were dissolved in 20 ml of dry THF. The solution was stirred at 0° C. and 25 ml of a 1.0M solution of $BH_3$ in THF was added. The temperature is left to return to ambient temperature and the reaction mixture is left stirring at ambient temperature for 5 h. The reaction mixture was carefully (drop by drop) acidified with 5 ml of 3N HCl (vigorous foaming and release of gas) and then brought to reflux for 0.5 h. After cooling to ambient temperature, the medium is alkalinized with a 1.0N aqueous solution of NaOH. The medium is then extracted several times with ethyl acetate. The organic phases were combined, and dried over $Na_2SO_4$. After filtration, the solvent was removed by evaporation. Addition of a small amount of diethyl ether resulted in crystallization.

The solid formed was dried by suction and, after drying under vacuum in the presence of a drying agent until a constant weight was obtained, the expected N,N-dimethyl-2-(7-nitro-3,4-dihydroquinolin-1(2H)-yl)ethanamine was isolated in the form of an orange powder (m.p. 126-128° C.).

The spectroscopic and spectrometric data are in accordance with the structure of the expected compound.

d) Synthesis of N,N,N-trimethyl-2-(7-nitro-3,4-dihydroquinolin-1(2H)-yl)ethanamonium-4-methylbenzenesulfonate

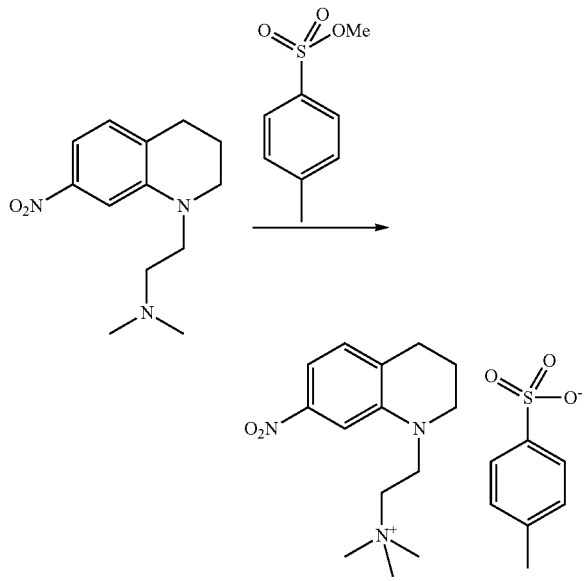

1 g (4 mmol) of N,N-dimethyl-2-(7-nitro-3,4-dihydroquinolin-1(2H)-yl)ethanamine and 3 ml (20 mmol) of methyl tosylate are introduced into a sealed tube and the tube is heated at 140° C. for 30 min. After cooling, the medium is taken up with dichloromethane and purified by column chromatography (dichloromethane-methanol gradient). N,N,N-trimethyl-2-(7-nitro-3,4-dihydroquinolin-1(2H)-yl)ethanamonium-4-methylbenzenesulfonate is thus isolated in the form of a yellow solid (m.p. 145-147° C.).

The spectroscopic and spectrometric data are in accordance with the structure of the expected compound.

e) Synthesis of 2-(7-amino-3,4-dihydroquinolin-1 (2H)-yl)-N,N,N-trimethylethanaminium chloride hydrochloride

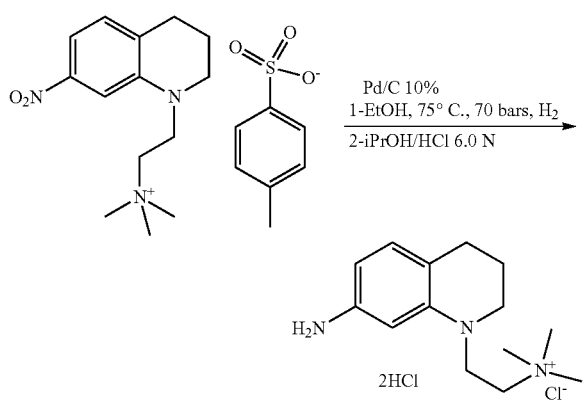

The reduction step is carried out using a hydrogenation system. A solution resulting from 3 g (6.88 mmol) of N,N,N-trimethyl-2-(7-nitro-3,4-dihydroquinolin-1(2H)-yl)ethanamonium 4-methylbenzenesulfonate in 78.5 ml of ethanol is introduced into the system equipped with a 90×4 mm cartridge of Pd/C 10%-type catalyst.

The reduction is carried out under the following conditions: pump flow rate 1.4 ml/min, temperature 80° C., pressure 70 bar and under a hydrogen flow rate of 125 ml/min.

On leaving the system, the reduced product is trapped with 100 ml of 6N iPrOH/HCl so as to form the hydrochloride, then the solvent is removed by evaporation under vacuum until an orange oil is obtained, which is taken up with 50 ml of isopropanol, and then the solution is again concentrated to approximately 30 ml, before being cooled to 0° C. with an ice bath. The crystallization is initiated with a glass rod. The white solid formed is then dried by suction on a sintered glass funnel, washed with 10 ml of isopropanol and 2×20 ml of diisopropyl ether, under an inert (argon) atmosphere, then taken up with 30 ml of diisopropyl ether, and dried by suction under an inert atmosphere (in the presence of argon) and then dried under vacuum at 45° C. in a desiccator in the presence of a drying agent until a constant weight of white solid corresponding to the expected product is obtained.

Examples of Dyeing

The following dyeing compositions are prepared:

| Examples | (A) | (B) | (C) |
|---|---|---|---|
| 2-(7-amino-3,4-dihydroquinolin-1(2H)-yl)-N,N,N-trimethylethanaminium chloride hydrochloride (example 1) | $10^{-3}$ mol | $10^{-3}$ mol | $10^{-3}$ mol |
| 2,3-diamino-6,7-dihydro-1H,5H-pyrazolo[1,2-a]pyrazol-1-one dimethanesulfonate | $10^{-3}$ mol | | |
| 2-[(3-aminopyrazolo[1,5-a]pyrid-2-yl)oxy]ethanol hydrochloride | | $10^{-3}$ mol | |
| 4-(3-aminopyrazolo[1,5-a]pyrid-2-yl)-1,1-dimethyl-piperazin-1-ium chloride hydrochloride | | | $10^{-3}$ mol |
| Dye support (1) Demineralized water qs | (*) 100 g | (*) 100 g | (*) 100 g |
| Shade observed | Chromatic bright coppery | Bright violet | Chromatic bright turquoise blue |

| | |
|---|---|
| 96° ethyl alcohol | 20.8 g |
| 35% aqueous sodium metabisulfite solution | 0.23 g AM |
| Pentasodium salt of diethylenetriaminepentaacetic acid as an aqueous 40% solution | 0.48 g AM |
| C$_8$-C$_{10}$ alkyl polyglucoside as an aqueous 60% solution | 3.6 g AM |
| Benzyl alcohol | 2.0 g |
| Polyethylene glycol containing 8 units of ethylene oxide | 3.0 g |
| NH$_4$Cl | 4.32 g |
| Aqueous ammonia containing 20% NH$_3$ | 2.94 g |

(*): dye support (1) pH 9.5

At the time of use, each composition is mixed with an equal weight of 20-volumes aqueous hydrogen peroxide solution (6% by weight). A final pH of 9.5 is obtained.

Each mixture obtained is applied to locks of grey hair containing 90% white hairs. After a leave-in time of 30 minutes, the locks are rinsed, washed with a standard shampoo, rinsed again and then dried.

The invention claimed is:

1. A method for dyeing keratin fibers comprising applying a cosmetic composition to said keratin fibers, said composition comprising:

at least one cationic heterocyclic coupler chosen from compounds of formula (I), salts thereof, optical or geometric isomers thereof, or solvates thereof:

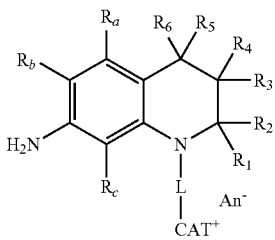

(I)

wherein:
$R_1$, $R_2$, $R_3$, $R_4$, $R_5$ and $R_6$ are independently chosen from:
  i) hydrogen or halogen atoms;
  ii) linear or branched $C_1$-$C_6$ alkyl radicals optionally substituted with one or more hydroxyl groups;
  iii) carboxyl radicals;
  iv) ($C_1$-$C_6$) alkoxycarbonyl radicals —C(O)—O—R, wherein R represents a linear or branched $C_1$-$C_6$ alkyl radical; and
  v) alkylcarbonyloxy radicals —O—C(O)—R wherein R represents a linear or branched $C_1$-$C_6$ alkyl radical;
$R_a$, $R_b$ and $R_c$ are independently chosen from hydrogen atoms, halogen atoms, and $C_1$-$C_6$ alkyl radicals;
L represents a saturated or unsaturated, linear or branched $C_1$-$C_{30}$, divalent hydrocarbon-based chain, optionally interrupted with one or more divalent groups or combinations thereof, wherein the divalent groups are chosen from —N($R_d$)—, —O—, —S—, —C(O)— and —S(O)$_2$—, wherein $R_d$ is chosen from hydrogen, $C_1$-$C_6$ alkyl radicals, hydroxy($C_1$-$C_6$)alkyl radicals, and amino($C_1$-$C_6$)alkyl radicals;
$CAT^+$ represents a cationic radical; and
$An^-$ represents one or more anionic counterions, wherein there are as many anionic counterion(s), which may be identical or different, as there are cationic charge(s) in order to ensure electroneutrality of the molecule of formula (I).

2. The method of claim 1, wherein the compound of formula (I) comprises radicals $R_1$, $R_2$, $R_3$, $R_4$, $R_5$ and $R_6$, independently chosen from hydrogen atoms or $C_1$-$C_4$ alkyl radicals.

3. The method of claim 1, wherein in the compound of formula (I), radicals $R_a$, $R_b$ and $R_c$ are chosen from hydrogen atoms.

4. The method of claim 1, wherein in the compound of formula (I), L is chosen from saturated, linear or branched, $C_1$-$C_{20}$ divalent hydrocarbon-based chains, optionally substituted with one or more hydroxyl radicals, and optionally interrupted with one or more non-adjacent heteroatoms chosen from oxygen or amino —N(R')—, wherein R' is chosen from hydrogen atoms or $C_1$-$C_6$ alkyl radicals.

5. The method of claim 1, wherein $CAT^+$ is a cationic radical chosen from:
monocyclic or polycyclic, saturated or unsaturated, aromatic or nonaromatic, cationic heterocyclic radicals, optionally substituted with one or more radicals independently chosen from linear or branched $C_1$-$C_4$ alkyl radicals or $C_1$-$C_4$ hydroxyalkyl radicals;
ammonium radicals $R_7R_8R_9N^+$, wherein $R_7$, $R_8$ and $R_9$ are independently chosen from linear or branched ($C_1$-$C_6$) alkyl groups, optionally substituted with one or more hydroxyl groups; and
aryl radicals with an exocyclic cationic charge.

6. The method of claim 1, wherein $CAT^+$ is chosen from monocyclic or bicyclic, saturated or unsaturated, aromatic or nonaromatic, heterocyclic cationic radicals, optionally substituted with one or more radicals independently chosen from linear or branched $C_1$-$C_4$ alkyl radicals or $C_1$-$C_4$ hydroxyalkyl radicals.

7. The method of claim 5, wherein the heterocyclic radicals comprise one or more endocyclic cationic charges, substituted on at least one heteroatom with one or two ($C_1$-$C_4$)alkyl groups.

8. The method of claim 5, wherein $CAT^+$ is chosen from tri(hydroxy)($C_1$-$C_4$)alkylammonium groups.

9. The method of claim 5, wherein $CAT^+$ represents an aryl group substituted with an ammonium group $B_7B_8R_9N^+$, wherein $R_7$, $R_8$ and $R_9$ are independently chosen from linear or branched ($C_1$-$C_6$)alkyl groups, optionally substituted with one or more hydroxyl groups.

10. The method of claim 1, wherein the at least one cationic heterocyclic coupler is chosen from compounds of formula (II):

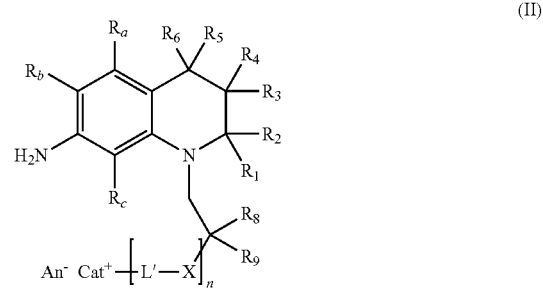

(II)

wherein:
$R_a$, $R_b$, $R_c$, $R_1$, $R_2$, $R_3$, $R_4$, $R_5$ and $R_6$ and $CAT^+$ and $An^-$ are as defined according to claim 1;
$R_8$ and $R_9$ independently represent hydrogen atoms or linear or branched $C_1$-$C_6$ alkyl radicals, optionally substituted with an —OH or interrupted with an oxygen atom;
X represents an oxygen atom or an —N(R')— radical wherein R' represents hydrogen atoms or $C_1$-$C_4$ alkyl radicals;
L' represents linear or branched and saturated divalent $C_1$-$C_{10}$ hydrocarbon-based chains, optionally substituted with one or more hydroxyl radicals; and
n is 0, 1, 2, 3 or 4;
wherein when n is greater than or equal to 2, the radicals L' and X respectively are identical or different.

11. The method of claim 1, wherein the compound of formula (I) is chosen from the following compounds:

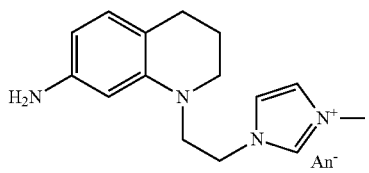

Salt of 1-[2-(7-amino-3,4-dihydroquinolin-1(2H)-yl)ethyl]-3-methyl-1H-imidazol-3-ium, An⁻

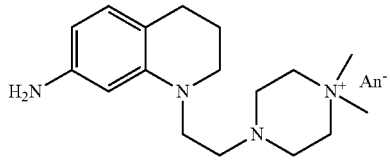

Salt of 4-[2-(7-amino-3,4-dihydroquinolin-1(2H)-yl)ethyl]-1,1-dimethylpiperazin-1-ium, An⁻

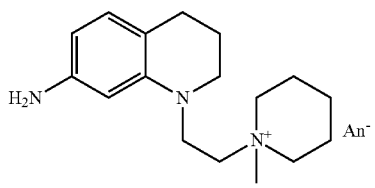

Salt of 1-[2-(7-amino-3,4-dihydroquinolin-1(2H)-yl)ethyl]-1-methylpiperidinium, An⁻

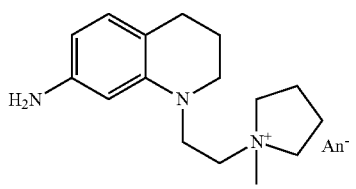

Salt of 1-[2-(7-amino-3,4-dihydroquinolin-1(2H)-yl)ethyl]-1-methylpyrrolidinium, An⁻

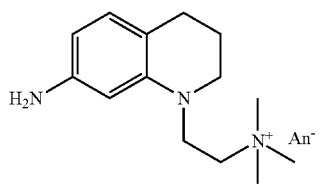

Salt of 2-(7-amino-3,4-dihydroquinolin-1(2H)-yl)-N,N,N-trimethylethanaminium, An⁻

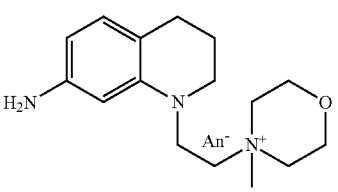

Salt of 4-[2-(7-amino-3,4-dihydroquinolin-1(2H)-yl)ethyl]-4-methylmorpholin-4-ium, An⁻

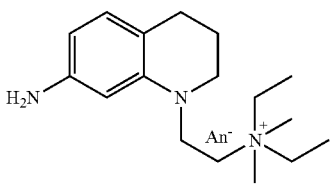

Salt of 2-(7-amino-3,4-dihydroquinolin-1(2H)-yl)-N,N,-diethyl-N-methylethanaminium, An⁻

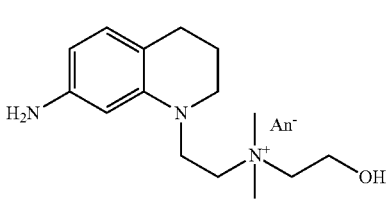

Salt of 2-(7-amino-3,4-dihydroquinolin-1(2H)-yl)-N-(2-hydroxyethyl)-N,N-dimethylethanaminium, An⁻

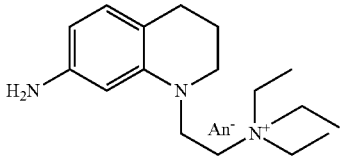

Salt of 2-(7-amino-3,4-dihydroquinolin-1(2H)-yl)-N,N,N-triethylethanaminium, An⁻

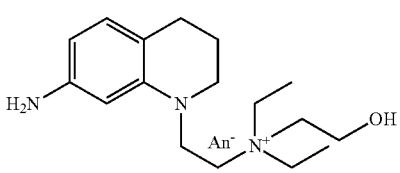

Salt of 2-(7-amino-3,4-dihydroquinolin-1(2H)-yl)-N,N-diethyl-N-(2-hydroxyethyl)ethanaminium, An⁻

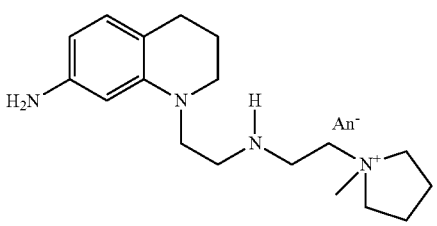

Salt of 1-(2-{[2-(7-amino-3,4-dihydroquinolin-1(2H)-yl)ethyl]amino}ethyl)-1-methylpyrrolidinium, An⁻

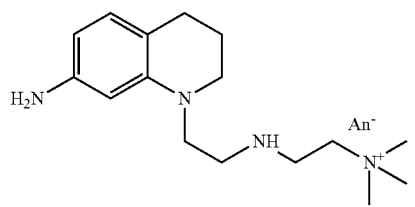

Salt of 2-{[2-(7-amino-3,4-dihydroquinolin-1(2H)-yl)ethyl]amino}-N,N,N-trimethylethanaminium, An⁻

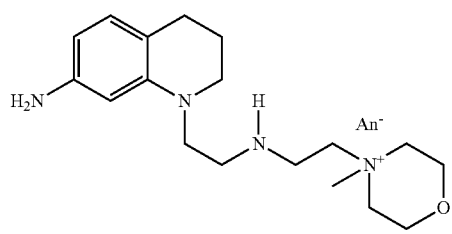

Salt of 4-(2-{[2-(7-amino-3,4-dihydroquinolin-1(2H)-yl)ethyl]amino}ethyl-4-methylmorpholin-4-ium, An⁻

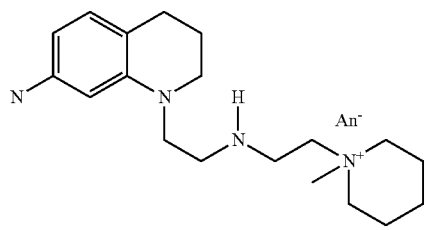

Salt of 1-(2-{[2-(7-amino-3,4-dihydroquinolin-1(2H)-yl)ethyl]amino}ethyl-1-methylpiperidinium, An⁻

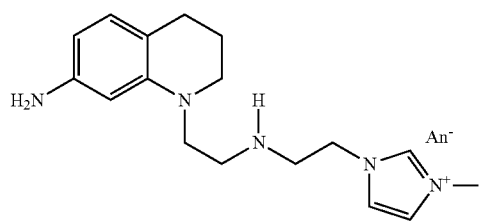

Salt of 1-(2-{[2-(7-amino-3,4-dihydroquinolin-1(2H)-yl)ethyl]amino}ethyl-3-methyl-1H-imidazol-3-ium, An⁻

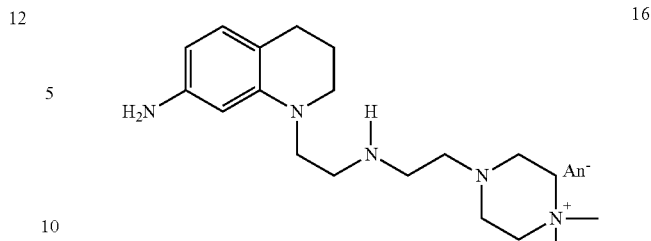

Salt of 4-(2-{[2-(7-amino-3,4-dihydroquinolin-1(2H)-yl)ethyl]amino}ethyl)-1,1-dimethylpiperazin-1-ium, An⁻

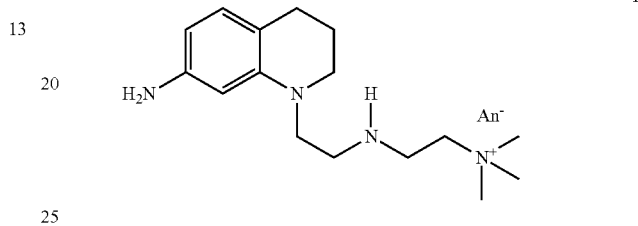

Salt of 3-{[2-(7-amino-3,4-dihydroquinolin-1(2H)-yl)ethyl]amino}-N,N,N-trimethylpropan-1-aminium, An⁻

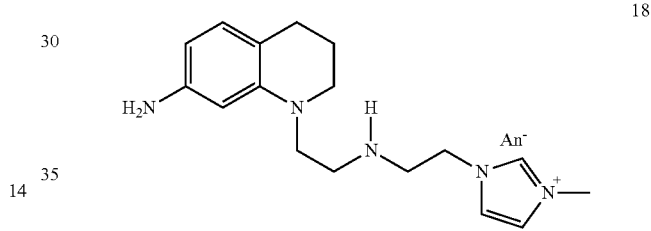

Salt of 1-(3-{[2-(7-amino-3,4-dihydroquinolin-1(2H)-yl)ethyl]amino}propyl)-3-methyl-1H-imidazol-3-ium, An⁻

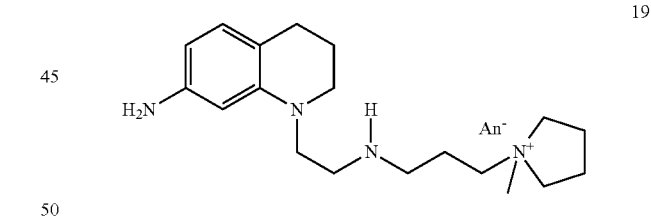

Salt of 1-(3-{[2-(7-amino-3,4-dihydroquinolin-1(2H)-yl)ethyl]amino}propyl)-1-methylpyrrolidinium, An⁻

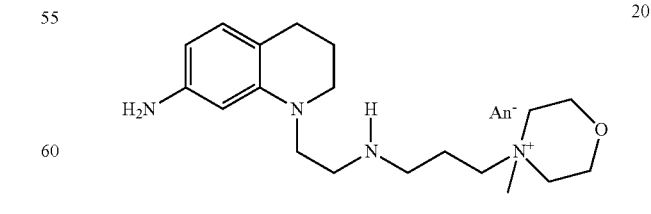

Salt of 4-(3-{[2-(7-amino-3,4-dihydroquinolin-1(2H)-yl)ethyl]amino}propyl)-4-methylmorpholin-4-ium, An⁻

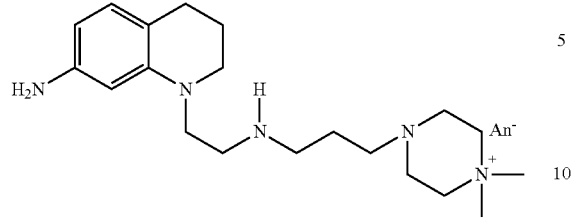

Salt of 4-(3-{[2-(7-amino-3,4-dihydroquinolin-1(2H)-yl)ethyl]amino}propyl)-1,1-dimethylpiperazin-1-ium, An⁻

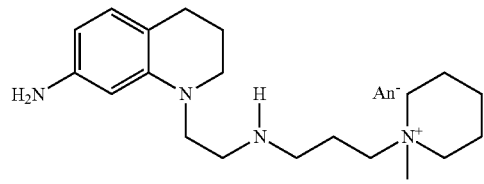

Salt of 1-(3-{[2-(7-amino-3,4-dihydroquinolin-1(2H)-yl)ethyl]amino}propyl)-1-methylpiperidinium, An⁻

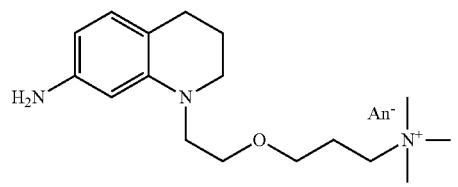

Salt of -3-[2-(7-amino-3,4-dihydroquinolin-1(2H)-yl)ethoxy]-N,N,N-trimethylpropan-1-aminium, An⁻

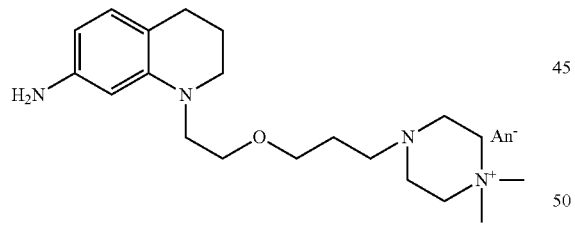

Salt of 4-{3-[2-(7-amino-3,4-dihydroquinolin-1(2H)-yl)ethoxy]propyl}-1,1-dimethylpiperazin-1-ium, An⁻

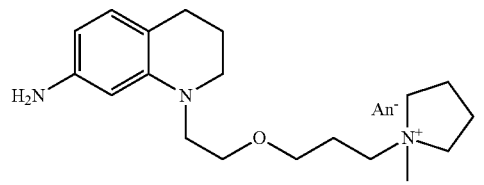

Salt of 11-{3-[2-(7-amino-3,4-dihydroquinolin-1(2H)-yl)ethoxy]propyl}-1-methylpyrrolidinium, An⁻

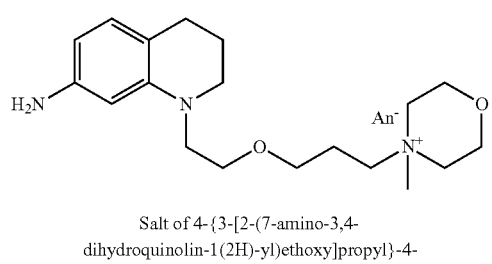

Salt of 4-{3-[2-(7-amino-3,4-dihydroquinolin-1(2H)-yl)ethoxy]propyl}-4-methylmorpholin-4-ium, An⁻

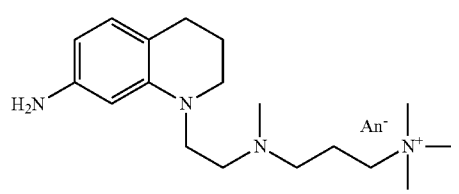

Salt of 3-{[2-(7-amino-3,4-dihydroquinolin-1(2H)-yl)ethyl](methyl)amino}-N,N,N-trimethylpropan-1-aminium, An⁻

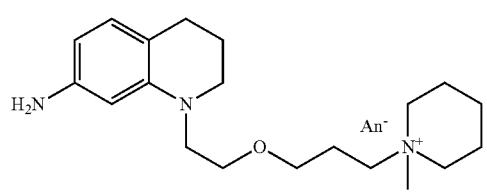

Salt of 1-{3-[2-(7-amino-3,4-dihydroquinolin-1(2H)-yl)ethoxy]propyl}-1-methylpiperidinium, An⁻

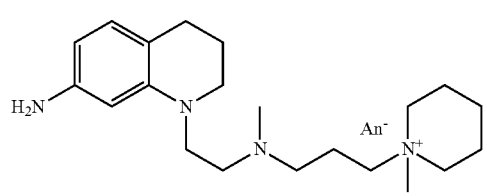

Salt of 1-(3-{[2-(7-amino-3,4-dihydroquinolin-1(2H)-yl)-2-oxoethyl](methyl)amino}propyl)-1-methylpiperidinium, An⁻

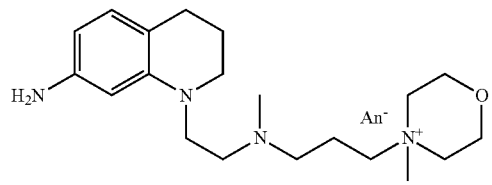

Salt of 4-(3-{[2-(7-amino-3,4-dihydroquinolin-1(2H)-yl)ethyl](methyl)amino}propyl)-4-methylmorpholin-4-ium, An⁻

-continued

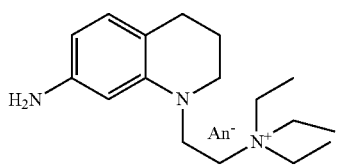

Salt of 2-(7-amino-3,4-dihydroquinolin-1(2H)-yl)-N,N,N-triethylethanaminium, An⁻

31

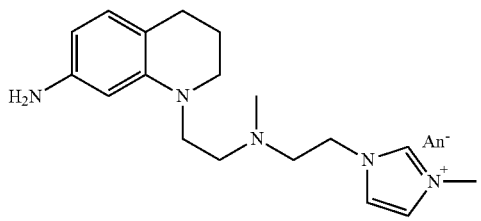

Salt of 1-(2-{[2-(7-amino-3,4-dihydroquinolin-1(2H)-2-oxoethyl(methyl)amino}ethyl)-3-methyl-1H-imidazol-3-ium, An⁻

32

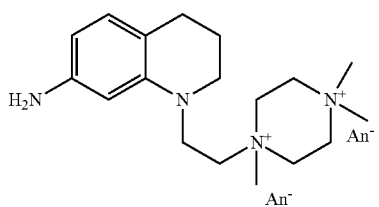

Salt of 1-[2-(7-amino-3,4-dihydroquinolin-1(2H)yl)ethyl]-1,4,4-trimethylpiperazinediium, An⁻

33 wherein An⁻ may independently be chosen from anionic counterions, salts thereof with organic or inorganic acids or bases, and/or solvates thereof.

12. A process for dyeing keratin fibers, said process comprising treating said fibers with at least one compound of formula (I), salts thereof, optical or geometric isomers thereof, or solvates thereof:

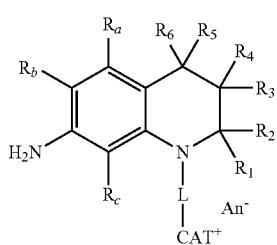

(I)

wherein:
$R_1$, $R_2$, $R_3$, $R_4$, $R_5$ and $R_6$ are independently chosen from:
  i) hydrogen or halogen atoms;
  ii) linear or branched $C_1$-$C_6$ alkyl radicals optionally substituted with one or more hydroxyl groups;
  iii) carboxyl radicals;
  iv) ($C_1$-$C_6$) alkoxycarbonyl radicals —C(O)—O—R, wherein R represents a linear or branched $C_1$-$C_6$ alkyl radical; and
  v) alkylcarbonyloxy radicals —O—C(O)—R wherein R represents a linear or branched $C_1$-$C_6$ alkyl radical;
$R_a$, $R_b$ and $R_c$ are independently chosen from hydrogen atoms, halogen atoms, and $C_1$-$C_6$ alkyl radicals;
L represents a saturated or unsaturated, linear or branched $C_1$-$C_{30}$, divalent hydrocarbon-based chain, optionally interrupted with one or more divalent groups or combinations thereof, wherein the divalent groups are chosen from —N($R_d$)—, —O—, —S—, —C(O)— and —S(O)$_2$—, wherein $R_d$ is chosen from hydrogen, $C_1$-$C_6$ alkyl radicals, hydroxy($C_1$-$C_6$)alkyl radicals, and amino($C_1$-$C_6$)alkyl radicals;
CAT⁺ represents a cationic radical; and
An⁻ represents one or more anionic counterions, wherein there are as many anionic counterion(s), which may be identical or different, as there are cationic charge(s) in order to ensure electroneutrality of the molecule of formula (I),
wherein the step of treating said fibers is performed in the presence of at least one oxidation base and at least one oxidizing agent, for a time sufficient to develop the desired coloration,
and wherein the oxidizing agent is applied before, simultaneously with, or after the application of the at least one compound of formula (I) and the at least one oxidation base.

13. A compound of formula (I), salts thereof, optical or geometric isomers thereof, or solvates thereof:

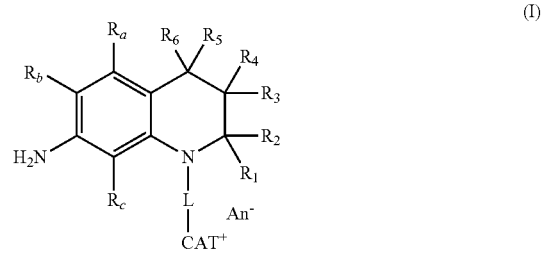

(I)

wherein:
$R_1$, $R_2$, $R_3$, $R_4$, $R_5$ and $R_6$ are independently chosen from:
  i) hydrogen or halogen atoms;
  ii) linear or branched $C_1$-$C_6$ alkyl radicals optionally substituted with one or more hydroxyl groups;
  iii) carboxyl radicals;
  iv) ($C_1$-$C_6$) alkoxycarbonyl radicals —C(O)—O—R, wherein R represents a linear or branched $C_1$-$C_6$ alkyl radical; and
  v) alkylcarbonyloxy radicals —O—C(O)—R wherein R represents a linear or branched $C_1$-$C_6$ alkyl radical;
$R_a$, $R_b$ and $R_c$ are independently chosen from hydrogen atoms, halogen atoms, and $C_1$-$C_6$ alkyl radicals;
L represents a saturated or unsaturated, linear or branched $C_1$-$C_{30}$, divalent hydrocarbon-based chain, optionally interrupted with one or more divalent groups or combinations thereof, wherein the divalent groups are chosen from —N($R_d$)—, —O—, —S—, —C(O)— and —S(O)$_2$—, wherein $R_d$ is chosen from hydrogen, $C_1$-$C_6$ alkyl radicals, hydroxy($C_1$-$C_6$)alkyl radicals, and amino($C_1$-$C_6$)alkyl radicals;

CAT$^+$ represents a cationic radical; and

An$^-$ represents one or more anionic counterions, wherein there are as many anionic counterion(s), which may be identical or different, as there are cationic charge(s) in order to ensure electroneutrality of the molecule of formula (I).

14. A cosmetic composition comprising:
a. at least one compound of formula (I), salts thereof, optical or geometric isomers thereof, or solvates thereof:

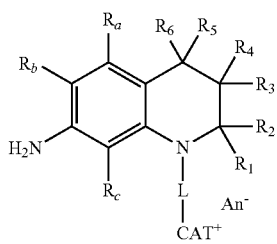

(I)

wherein:
$R_1$, $R_2$, $R_3$, $R_4$, $R_5$ and $R_6$ are independently chosen from:
  i) hydrogen or halogen atoms;
  ii) linear or branched $C_1$-$C_6$ alkyl radicals optionally substituted with one or more hydroxyl groups;
  iii) carboxyl radicals;
  iv) ($C_1$-$C_6$) alkoxycarbonyl radicals —C(O)—O—R, wherein R represents a linear or branched $C_1$-$C_6$ alkyl radical; and
  v) alkylcarbonyloxy radicals —O—C(O)—R wherein R represents a linear or branched $C_1$-$C_6$ alkyl radical;
$R_a$, $R_b$ and $R_c$ are independently chosen from hydrogen atoms, halogen atoms, and $C_1$-$C_6$ alkyl radicals;
L represents a saturated or unsaturated, linear or branched $C_1$-$C_{30}$, divalent hydrocarbon-based chain, optionally interrupted with one or more divalent groups or combinations thereof, wherein the divalent groups are chosen from —N($R_d$)—, —O—, —S—, —C(O)— and —S(O)$_2$—, wherein $R_d$ is chosen from hydrogen, $C_1$-$C_6$ alkyl radicals, hydroxy($C_1$-$C_6$)alkyl radicals, and amino($C_1$-$C_6$)alkyl radicals;
CAT$^+$ represents a cationic radical; and
An$^-$ represents one or more anionic counterions, wherein there are as many anionic counterion(s), which may be identical or different, as there are cationic charge(s) in order to ensure electroneutrality of the molecule of formula (I);
b. optionally at least one oxidation base; and
c. optionally at least one oxidizing agent.

15. A multi-compartment device comprising:
a first compartment containing cosmetic composition comprising:
a. at least one compound of formula (I), salts thereof, optical or geometric isomers thereof, or solvates thereof:

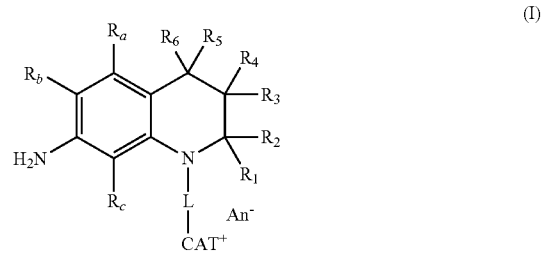

(I)

wherein:
$R_1$, $R_2$, $R_3$, $R_4$, $R_5$ and $R_6$ are independently chosen from:
  i) hydrogen or halogen atoms;
  ii) linear or branched $C_1$-$C_6$ alkyl radicals optionally substituted with one or more hydroxyl groups;
  iii) carboxyl radicals;
  iv) ($C_1$-$C_6$) alkoxycarbonyl radicals —C(O)—O—R, wherein R represents a linear or branched $C_1$-$C_6$ alkyl radical; and
  v) alkylcarbonyloxy radicals —O—C(O)—R wherein R represents a linear or branched $C_1$-$C_6$ alkyl radical;
$R_a$, $R_b$ and $R_c$ are independently chosen from hydrogen atoms, halogen atoms, and $C_1$-$C_6$ alkyl radicals;
L represents a saturated or unsaturated, linear or branched $C_1$-$C_{30}$, divalent hydrocarbon-based chain, optionally interrupted with one or more divalent groups or combinations thereof, wherein the divalent groups are chosen from —N($R_d$)—, —O—, —S—, —C(O)— and —S(O)$_2$—, wherein $R_d$ is chosen from hydrogen, $C_1$-$C_6$ alkyl radicals, hydroxy($C_1$-$C_6$)alkyl radicals, and amino($C_1$-$C_6$)alkyl radicals;
CAT$^+$ represents a cationic radical; and
An$^-$ represents one or more anionic counterions, wherein there are as many anionic counterion(s), which may be identical or different, as there are cationic charge(s) in order to ensure electroneutrality of the molecule of formula (I); and
b. optionally at least one oxidation base;
wherein said first compartment is free of any oxidizing agent, and
a second compartment containing at least one oxidizing agent.

* * * * *

UNITED STATES PATENT AND TRADEMARK OFFICE
CERTIFICATE OF CORRECTION

| | |
|---|---|
| PATENT NO. | : 9,107,848 B2 |
| APPLICATION NO. | : 14/365726 |
| DATED | : August 18, 2015 |
| INVENTOR(S) | : Azia Fadli |

It is certified that error appears in the above-identified patent and that said Letters Patent is hereby corrected as shown below:

Claims

Col. 36, line 23, Claim 9, "B7B8R9N+" should be -- R7R8R9N+ --.

Signed and Sealed this
Twenty-second Day of December, 2015

Michelle K. Lee
*Director of the United States Patent and Trademark Office*